US011812968B2

(12) United States Patent
Li et al.

(10) Patent No.: US 11,812,968 B2
(45) Date of Patent: Nov. 14, 2023

(54) LEFT ATRIAL APPENDAGE OCCLUDER

(71) Applicant: Lifetech Scientific (Shenzhen) Co., Ltd., Shenzhen (CN)

(72) Inventors: Anning Li, Shenzhen (CN); Zhuo Chen, Shenzhen (CN)

(73) Assignee: Lifetech Scientific (Shenzhen) Co. Ltd., Shenzhen (CN)

(*) Notice: Subject to any disclaimer, the term of this patent is extended or adjusted under 35 U.S.C. 154(b) by 671 days.

(21) Appl. No.: 16/823,718

(22) Filed: Mar. 19, 2020

(65) Prior Publication Data
US 2020/0214714 A1 Jul. 9, 2020

Related U.S. Application Data

(63) Continuation of application No. 15/525,907, filed on May 10, 2017, now Pat. No. 10,624,648.

(51) Int. Cl.
*A61B 17/12* (2006.01)
*A61B 17/00* (2006.01)

(52) U.S. Cl.
CPC ........ *A61B 17/12122* (2013.01); *A61B 17/00* (2013.01); *A61B 17/0057* (2013.01);
(Continued)

(58) Field of Classification Search
CPC .......... A61B 17/0057; A61B 17/12122; A61B 17/12168; A61B 17/00; A61B 2017/00597; A61B 2017/00632
See application file for complete search history.

(56) References Cited

U.S. PATENT DOCUMENTS 6,152,144 A   11/2000 Lesh et al.
6,375,668 B1* 4/2002 Gifford ............ A61B 17/12022
                                                          606/200
(Continued)

FOREIGN PATENT DOCUMENTS

CN   101384294 A   3/2009
CN   102908174 A   2/2013
(Continued)

OTHER PUBLICATIONS

Office Action dated Apr. 14, 2021 for corresponding New Zealand Application No. 731527.
(Continued)

*Primary Examiner* — George J Ulsh
(74) *Attorney, Agent, or Firm* — Raymond Sun

(57) ABSTRACT

A left atrial appendage occluder (200) comprises a sealing part (220), a fixing part (210) disposed at one side of the sealing part (220), and a connection part (230) for connecting the sealing part (220) and the fixing part (210). The radial deformation capacity of the sealing part (220) is greater than the radial deformation capacity of the fixing part (210), and/or, the axial deformation capacity of the sealing part (220) is greater than the axial deformation capacity of the fixing part (210). In the left atrial appendage occluder (200), the radial or axial deformation capacity of the sealing part (220) is configured to be greater than the radial or axial deformation capacity of the fixing part (210), thereby avoiding the situation in which the sealing part (220) is not optimally fitted with the opening of the left atrial appendage (10) when the fixing part (210) is placed inside of the left atrial appendage (10), which in turn enhances the occlusion effect. Additionally, the sealing part (220) has great deformation capacity which reduces the risks of the sealing part (220) causing abrasion to the opening of the left atrial appendage, or even damaging the opening of the left atrial
(Continued)

appendage. The fixing part (210) not only avoids the risks, but also fixes the occluder in the left atrial appendage (10) more effectively, and prevents the occluder (200) from being disengaged from the left atrial appendage.

20 Claims, 14 Drawing Sheets

(52) U.S. Cl.
CPC .............. *A61B 17/12168* (2013.01); *A61B 2017/00597* (2013.01); *A61B 2017/00632* (2013.01)

(56) References Cited

U.S. PATENT DOCUMENTS

| | | | |
|---|---|---|---|
| 9,259,337 B2* | 2/2016 | Cox | A61B 17/12172 |
| 9,314,326 B2* | 4/2016 | Wallace | A61B 17/12172 |
| 2009/0171386 A1* | 7/2009 | Amplatz | A61B 17/0057 |
| | | | 606/213 |
| 2011/0144669 A1* | 6/2011 | Becking | A61B 17/12022 |
| | | | 606/158 |
| 2011/0208233 A1* | 8/2011 | McGuckin, Jr. | ............ |
| | | | A61B 17/12186 |
| | | | 606/200 |
| 2012/0172927 A1* | 7/2012 | Campbell | A61B 17/12122 |
| | | | 606/213 |
| 2013/0131717 A1* | 5/2013 | Glimsdale | A61B 17/12172 |
| | | | 606/213 |
| 2013/0218193 A1* | 8/2013 | Erzberger | A61B 17/12122 |
| | | | 606/200 |
| 2014/0005714 A1* | 1/2014 | Quick | A61B 17/12122 |
| | | | 606/200 |
| 2014/0142612 A1* | 5/2014 | Li | A61B 17/12172 |
| | | | 606/200 |
| 2017/0095256 A1* | 4/2017 | Lindgren | A61B 17/12172 |
| 2017/0367708 A1* | 12/2017 | Mayer | A61B 17/12036 |

FOREIGN PATENT DOCUMENTS

| | | |
|---|---|---|
| CN | 103209649 A | 7/2013 |
| WO | WO2015/189307 A1 | 6/2015 |

OTHER PUBLICATIONS

Office Action dated Mar. 31, 2021 for corresponding China Application No. 201910569067.X.
Office Action dated Apr. 14, 2021 for corresponding China Application No. 201580069864.1.
English translation for Office Action dated Nov. 4, 2020 for corresponding China Application No. 201580069864.1.
Office Action dated Nov. 4, 2020 for corresponding China Application No. 201580069864.1.

* cited by examiner

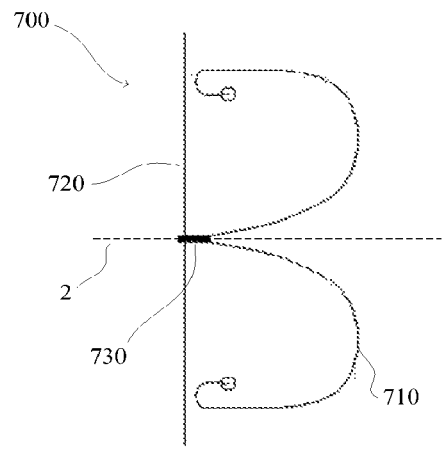
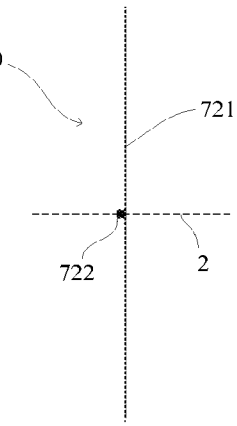
Figure11
Figure12
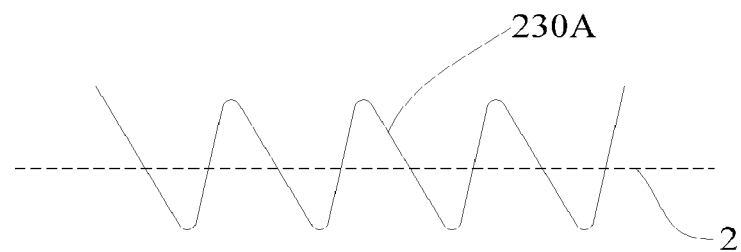
Figure13
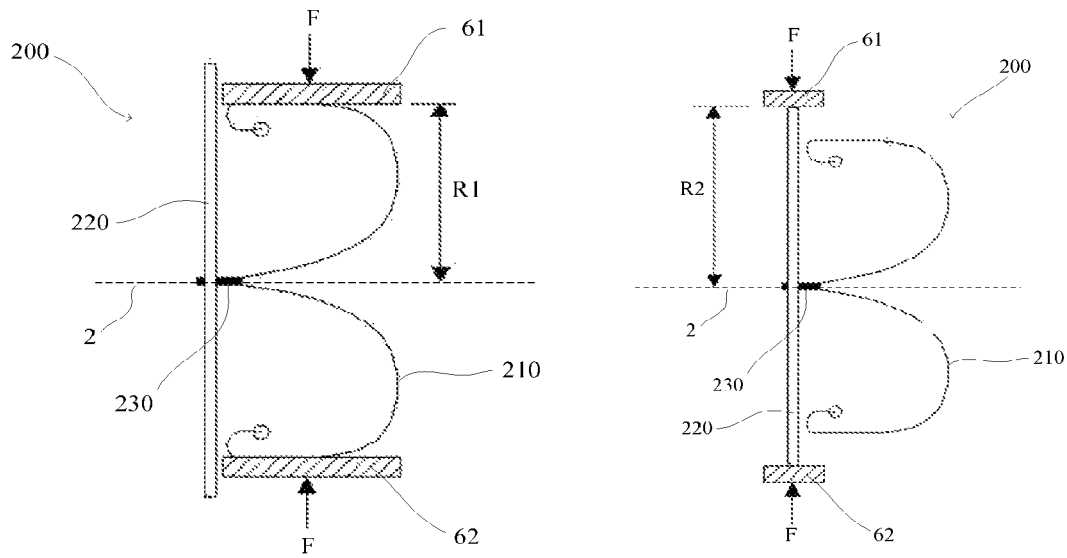
Figure14
Figure15

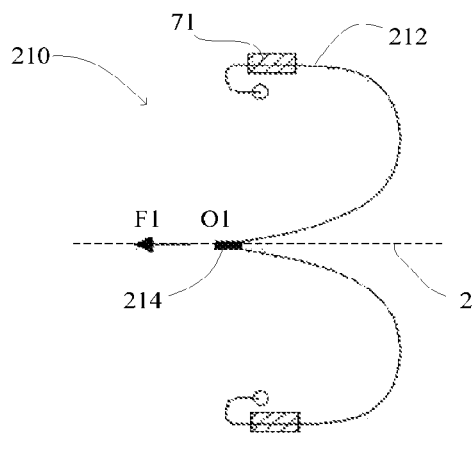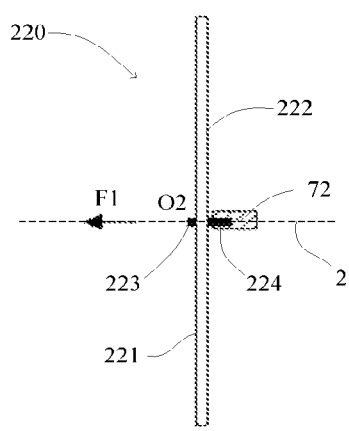
Figure27  Figure28
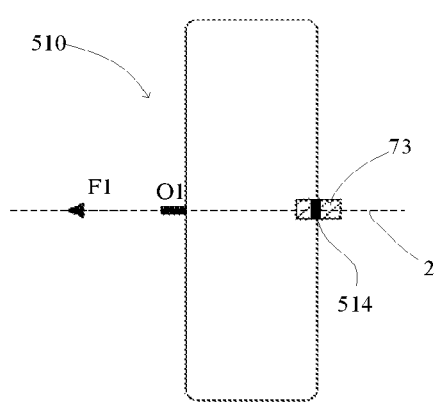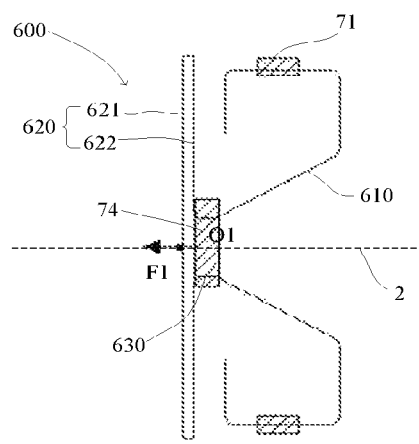
Figure29  Figure30
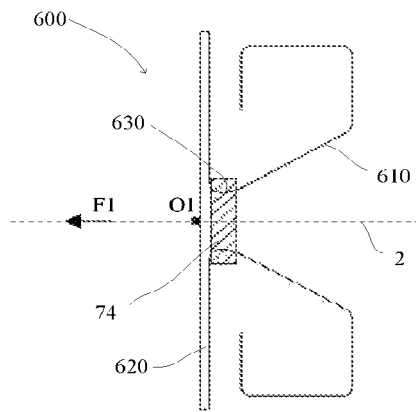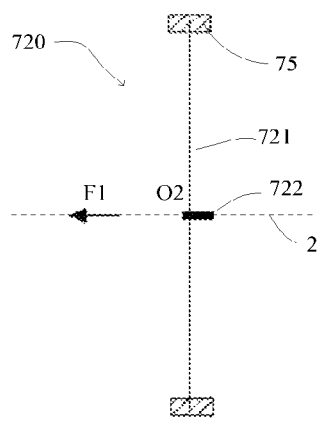
Figure31  Figure32

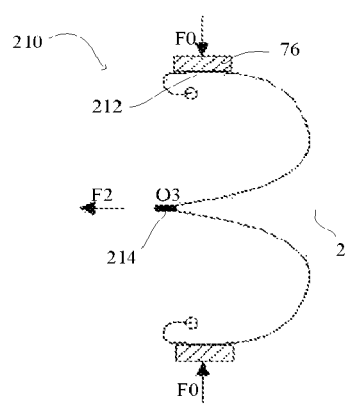
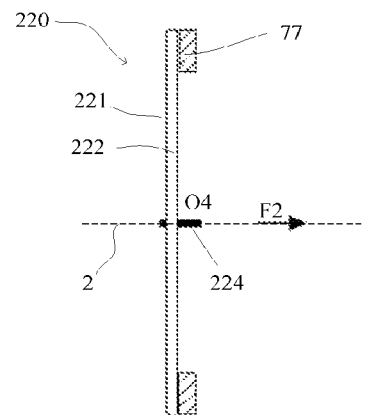
Figure33　　　　　　　　　　Figure34
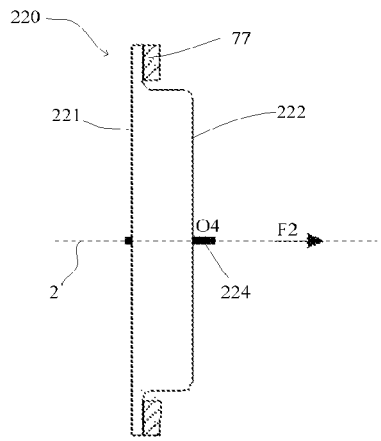
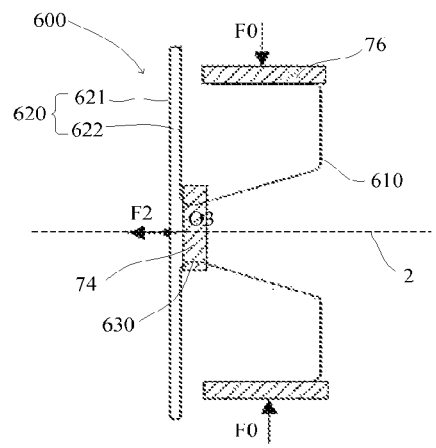
Figure35　　　　　　　　　　Figure36
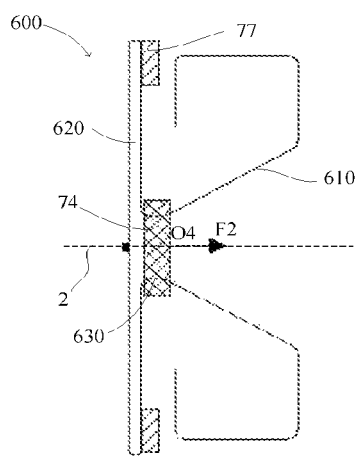
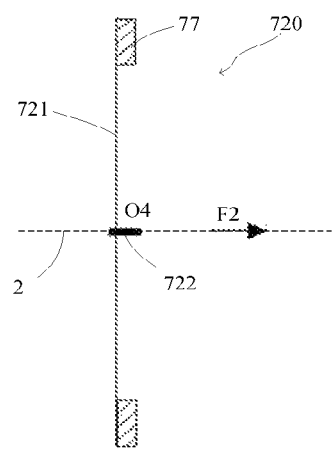
Figure37　　　　　　　　　　Figure38

LEFT ATRIAL APPENDAGE OCCLUDER

TECHNICAL FIELD

The present disclosure relates to a medical device, and particularly relates to a left atrial appendage occluder.

BACKGROUND

At present, an occluder can be placed into the left atrial appendage by a catheter-based interventional method to prevent thrombus of the left atrial appendage due to atrial fibrillation from ascending into the brain and then causing a stroke; or to avoid systemic embolism caused by the thrombus reaching other parts of the body through the blood circulation system of a human body. Such left atrial appendage occluders may generally include integrated type and split type in structure. For example, a split occluder usually comprises a fixing part and a sealing part which are connected to each other, wherein the fixing part is placed in the cavity of a left atrial appendage to fix the whole occluder, and the sealing part seals the opening of a left atrial appendage to block the blood from flowing into the cavity of the left atrial appendage.

For such a split occluder, the fixing part and sealing part thereof are connected in a constrained manner, and cannot deform in a completely independent manner, so that one part will be pulled by the other part. For example, once fixed in the cavity of a left atrial appendage, the fixing part will pull the sealing part in the process of adapting to the cavity structure of the left atrial appendage and the activity of the left atrial appendage. This pulling may cause the sealing part to not fully fit the opening of the left atrial appendage, thereby forming a blood leakage passage between the left atrium and the left atrial appendage, so that the device is unable to seal the opening optimally and thus allowing the thrombus in the left atrial appendage to flow out therefrom to possibly cause a stroke.

SUMMARY OF THE INVENTION

The present disclosure provides a left atrial appendage occluder to solve the technical problem in view of the defects in the prior art.

The technical solution employed by the present disclosure to solve the technical problem thereof is to provide a left atrial appendage occluder comprising a sealing part, a fixing part disposed at one side of the sealing part, and a connection part for connecting the sealing part and the fixing part; and the radial deformation capacity of the sealing part is greater than the radial deformation capacity of the fixing part, and/or, the axial deformation capacity of the sealing part is greater than the axial deformation capacity of the fixing part.

In the left atrial appendage occluder according to an embodiment of the present disclosure, under the action of the same radial force, a radial length variation of the sealing part is greater than that of the fixing part, or a radial length variation ratio of the sealing part is greater than that of the fixing part.

In the left atrial appendage occluder according to an embodiment of the present disclosure, under the same axial force, the displacement of the sealing part along the direction of the axial force is greater than that of the fixing part.

In the left atrial appendage occluder according to an embodiment of the present disclosure, the sealing part comprises a plurality of braid wires and a fixed connecting part; wherein the distal ends of the plurality of braid wires are fixedly connected with the connection part respectively, and the proximal ends of the plurality of braid wires are received and fixed by the fixed connecting part respectively. The sealing part comprises a disc-shaped portion adjoined to the fixed connecting part, and a transition portion extending between the disc-shaped portion and the proximal end of the fixed connecting part.

In the left atrial appendage occluder according to an embodiment of the present disclosure, the sealing part further comprises a sealing cap covering the transition portion and fixed to the proximal end of the fixed connecting part.

In the left atrial appendage occluder according to an embodiment of the present disclosure, the sealing cap comprises an end cap, and a sidewall connected with the end cap; and the sidewall extends in an arc shape from the proximal end to the distal end, and the end cap is fixed to the proximal end of the fixed connecting part.

In the left atrial appendage occluder according to an embodiment of the present disclosure, the equivalent diameter of the sealing cap is 2-5 mm.

In the left atrial appendage occluder according to an embodiment of the present disclosure, the surface of the proximal end of the disc-shaped portion is flat or concave.

In the left atrial appendage occluder according to an embodiment of the present disclosure, when the surface of the proximal end of the disc-shaped portion is a concave surface, the disc-shaped portion comprises a first flat surface adjoined to the fixed connection component, and an inclined surface connected with the first flat surface.

In the left atrial appendage occluder according to an embodiment of the present disclosure, the disc-shaped portion further comprises a second flat surface connected with the inclined surface.

In the left atrial appendage occluder according to an embodiment of the present disclosure, when the surface of the proximal end of the disc-shaped portion is a concave surface, the equivalent concave angle of the concave surface is less than 180 degrees.

In the left atrial appendage occluder according to an embodiment of the present disclosure, the number of the braid wires ranges from 12 to 168 or from 36 to 144; and the diameter of each braiding wire is 0.01 to 0.5 mm.

In the left atrial appendage occluder according to an embodiment of the present disclosure, the surface of the braiding wire is coated with a bioceramic film.

In the left atrial appendage occluder according to an embodiment of the present disclosure, the fixing part comprises a plurality of supporting members, wherein one end of each of the plurality of supporting members is fixedly connected with the connection part respectively and the other end includes a hung bearing section.

In the left atrial appendage occluder according to an embodiment of the present disclosure, each hung bearing section is provided with an anchor facing the sealing part, wherein an inclined angle between the anchor and the hung bearing section ranges from 0 degree to 90 degrees.

In the left atrial appendage occluder according to an embodiment of the present disclosure, each hung bearing section comprises a bearing portion and a bent end portion connected with the bearing portion.

In the left atrial appendage occluder according to an embodiment of the present disclosure, an included angle between the bearing portion and the central axis line of the left atrial appendage occluder ranges from 0 degree to 85 degrees; and an equivalent bend angle of the tail portion ranges from 0 degree to 180 degrees and the tail end of the tail portion is configured to a spherical structure.

In a left atrial appendage occluder according to an embodiment of the present disclosure, the relative distance between the proximal end of the sealing part and the distal end of the fixing part is 4-70 mm.

In the left atrial appendage occluder according to an embodiment of the present disclosure, an expanding diameter of the sealing part is greater than an expanding diameter of the fixing part.

In the left atrial appendage occluder according to an embodiments of the present disclosure, the radial or axial deformation capacity of the sealing part is set to be greater than the corresponding radial or axial deformation capacity of the fixing part, thereby preventing the situation that the sealing part cannot be optimally fitted with the opening of the left atrial appendage after the fixing part is placed in the left atrial appendage, which in turn enhances the occlusion effect. Meanwhile, owing to the great deformation capacity of the sealing part, risks of abrasion or damage to the opening of the left atrial appendage caused by the sealing part may be reduced.

BRIEF DESCRIPTION OF THE DRAWINGS

The present disclosure will be further described in detail below in combination with drawings and embodiments, and in the drawings:

FIG. 11 is a structural schematic diagram of a left atrial appendage occluder according to a sixth embodiment of the present disclosure:

FIG. 12 is a structural schematic diagram of the sealing part in FIG. 1I;

FIG. 13 is a structural schematic diagram of the connection part of a left atrial appendage occluder according to a seventh embodiment of the present disclosure:

FIGS. 14 and 15 are schematic diagrams for testing the left atrial appendage occluder of the first embodiment by using a first exemplary testing method:

FIGS. 15-18 are schematic diagrams for testing a liable deformation structure of the sealing part of the first embodiment by using the first exemplary testing method;

FIGS. 27 and 28 are schematic diagrams for testing the left atrial appendage occluder of the first embodiment by using a second exemplary testing method:

FIG. 29 is a schematic diagram for testing the fixing part of the left atrial appendage occluder of the fourth embodiment by using the second exemplary testing method:

FIGS. 30 and 31 are schematic diagrams for testing the left atrial appendage occluder of the fifth embodiment by using the second exemplary testing method:

FIG. 32 is a schematic diagram for testing the fixing part of the left atrial appendage occluder of the sixth embodiment by using the second exemplary testing method:

FIGS. 33-35 are schematic diagrams for testing the left atrial appendage occluder of the first embodiment by using a third exemplary testing method:

FIGS. 36 and 37 are schematic diagrams for testing the left atrial appendage occluder of the fifth embodiment by using the third exemplary testing method:

FIG. 38 is a schematic diagram for testing the sealing of the left atrial appendage occluder of the sixth embodiment by using the third exemplary testing method:

FIG. 2a is a structural schematic diagram of the left atrial appendage occluder in FIG. 1a:

FIG. 3a is a schematic diagram of a sealing part of the left atrial appendage occluder in FIG. 2a:

FIG. 4a is a partial enlarged figure of the sealing part in FIG. 3a:

FIG. 5a is a schematic diagram of the sealing cap in FIG. 3a:

FIG. 6a is a schematic diagram of the sealing cap in FIG. 3a:

FIG. 13a is a schematic diagram of supporting members in FIG. 12a;

DETAILED DESCRIPTION OF THE INVENTION

For the purpose of understanding the technical features, the purpose and the effect of the present disclosure more clearly, the detailed description of the present disclosure is described in detail with the accompanying drawings.

The left atrial appendage occluder (hereinafter referred to as the occluder) according to an embodiment of the present disclosure comprises a sealing part, a fixing part disposed at one side of the sealing part, and a connection part for connecting the sealing part and the fixing part, wherein the radial deformation capacity of the sealing part is greater than that of the fixing part, and/or the axial deformation capacity of the sealing part is greater than that of the fixing part. For convenience, proximal and distal positions are now defined. For example, the sealing part is disposed at one side of the proximal end of the fixing part, and the proximal end disc surface of the sealing part is provided with a fixed connecting part for connecting to an external delivery system. Various specific structures of the left atrial appendage occluder will be shown below. It should be appreciated that the following various occluder structures are just embodiments and not intended to limit the present disclosure, and the left atrial appendage occluders that are based on the teachings of the present disclosure all fall within the scope of the present disclosure.

After the left atrial appendage occluder according to the embodiments of the present disclosure is implanted into a human body, its fixing part spreads radially within a cavity of the left atrial appendage and clings tightly to the inner cavity wall of the left atrial appendage, and thus is fixed within the cavity of the left atrial appendage through its radial support force. Generally, what commonly clings tightly to the inner cavity wall of the left atrial appendage is the maximum radial contour of the fixing part, while the sealing part covers or directly plugs the opening of the left atrial appendage. When the size of the sealing part in a natural state is far bigger than the opening of the left atrial appendage, the sealing part is generally fixed outside of the opening through the traction of the fixing part, and the maximum radial edge region of the sealing part is pressed tightly to the left atrial wall at the opening to achieve the covering. When the size of the sealing part in its natural state is slightly bigger than or equal to the opening of the left atrial appendage, generally the sealing part is plugged directly into the opening. Through these two occlusion techniques, the blood in a left atrium is prevented from flowing into the cavity of a left atrial appendage, and thrombi are prevented from entering the left atrium from the left atrial appendage.

First Embodiment

Figure 1:
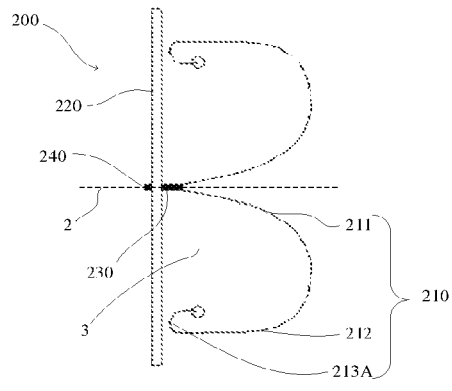
FIG. 1 is a structural schematic diagram of an exemplary left atrial appendage occluder according to a first embodiment of the present disclosure.
Figure 2:
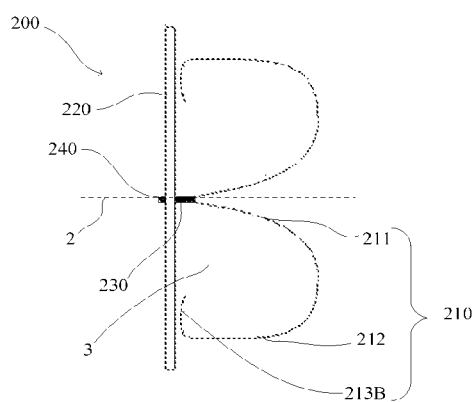
FIG. 2 is a structural schematic diagram of another exemplary left atrial appendage occluder according to the first embodiment of the present disclosure.

Referring to FIGS. 1-2, the left atrial appendage occluder 200 according to a first embodiment of the present disclosure has a central axis 2. A fixing part 210 of the left atrial appendage occluder 200 converges at one end and is connected with a connection part 230. Moreover, the fixing part 210 comprises a concave zone 211 formed by radially spreading from this end to a distal end, and a hung zone 212 formed through the extension from the concave zone 211 to a proximal end after bending, wherein the hung zone 212 defines an opening 3 towards the proximal end. The fixing part 210 may be braided integrally with braid wires. For example, the concave zone 211 and the hung zone 212 are braided bodies having a plurality of grids; and the fixing part 210 may also be formed by the cutting of metal tubes. For example, the concave zone 211 and the hung zone 212 respectively comprise a plurality of cut metal rod parts that may be connected with or spaced apart from one another. According to requirements or demands, such as those for making the deformation capacity of the fixing part smaller than that of the sealing part, those of ordinary skill in the art may choose suitable braid wires or metal tubes, such as nickel-titanium alloy; and furthermore, the wire diameters of braid wires, braiding methods, and so on, or the tube diameters, thicknesses of tube walls, cutting widths, and so on, of suitable metal tubes may be further chosen, which will not be described in greater detail herein.

In some specific implementations, the fixing part 210 further comprises an edge zone 213A formed through the bending and extension from the edge of the hung zone 212 to the central axis 2. The edge zone 213A will occupy a part of the opening 3, thereby blocking part of the opening 3. For example, the blocked opening 3 may be defined to be a fully opened opening 3, or a partially opened opening 3, according to a ratio of a projected area of the edge zone 213A on the maximum cross-section of the opening 3 to the area of the maximum cross-section of the opening 3, wherein, if the ratio is less than or equal to 10%, then the blocked opening 3 is a fully open opening 3; and if the ratio is greater than 10%, then the blocked opening 3 is a partially open opening 3. For example FIG. 1 illustrates the fully open opening 3 formed from the edge zone 213A, and FIG. 2 illustrates the partially open opening 3 formed from the edge zone 213B. It should be known that the cross-section of the opening 3 is perpendicular to the central axis 2, and as the opening 3 is defined by the hung zone 212, the cross-section of the opening 3 is formed by the maximum contour line of the hung zone 212 around the central axis 2; and the projected area of the edge zone 213A is defined by the projected contour line of the edge zone 213A around the central axis 2 on the cross-section of the above opening 3.

A sealing part 220 in this embodiment is a dual-layer disc, such as, a dual-layer sealed disc in which a proximal-side surface and a distal-side surface are connected together at an edge. The dual-layer disc is a dual-layer braided disc formed by heat setting of a braiding mesh tube or a dual-layer cut disc formed by cutting a nickel-titanium tube. The center of the proximal end of disc surface of the sealing part 220 is provided with a fixed connecting part 240 for connecting to an external delivery system. The connection part 230 may be any suitable structure, such as those with adjustable lengths or non-adjustable lengths.

Second Embodiment

Figure 3:
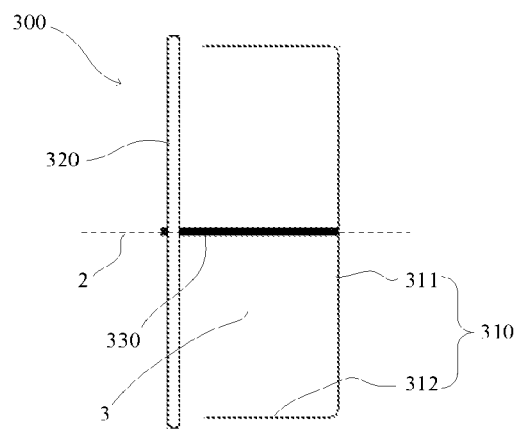
FIG. 3 is a structural schematic diagram of an exemplary left atrial appendage occluder according to a second embodiment of the present disclosure.
Figure 4:
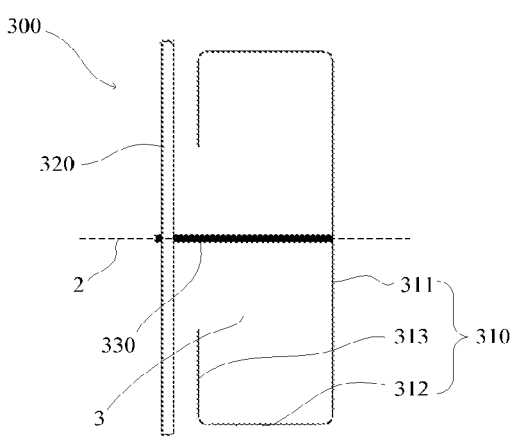
FIG. 4 is a structural schematic diagram of another exemplary left atrial appendage occluder according to the second embodiment of the present disclosure.

Referring to FIGS. 3-4, a difference between the left atrial appendage occluder 200 in the first embodiment and a left atrial appendage occluder 300 according to a second embodiment is that the distance between a distal end of a sealing part 320 of the left atrial appendage occluder 300 and a distal end of the fixing part 310 along the direction of a central axis 2 is basically equal to the length of a connection part 330 itself along the central axis 2. The connection part 330 may comprise a rod part and may comprise a braided body, and may further comprise a plurality of metal wires bound together, which will not be described in greater detail herein.

The fixing part 310 converges at an end portion and is connected with one end of the connection part 330, and the fixing part 310 comprises a distal end surface zone 311 formed by radially spreading from the end portion, and a hung zone 312 formed by extension from the distal end surface zone 311 to the proximal end after bending, wherein an opening 3 is defined by the hung zone 312 towards the proximal end. The fixing part 310 may be integrally braided with braid wires. For example, the hung zone 312 is a braided body having a plurality of grids. The fixing part 310 may also be formed by cutting a metal tube. For example, the hung zone 312 comprises a plurality of cut metal rod parts connected with or spaced apart from one another. Alternatively, the fixing part 310 and the connection part 330 respectively may be formed by integrated braiding or integrated cutting. According to requirements or demands, such as those for making the deformation capacity of the fixing part smaller than that of the sealing part, those of ordinary skill in the art may choose suitable braid wires or metal tubes, such as nickel-titanium alloy; and furthermore, the wire diameters of braid wires, braiding methods, and so on, or the tube diameters, thicknesses of tube walls, cutting widths, and so on, of suitable metal tubes may be further chosen, which will not described in greater detail herein.

Applying the definitions used for the first embodiment, the fixing part 310 in the second embodiment may form a fully opened opening 3 or a partially opened opening 3. For example, FIG. 3 illustrates the fixing part 310 with a fully opened opening 3, and FIG. 4 illustrates the fixing part 310 with a partially opened opening 3. The opening 3 is partially blocked by an edge zone 313 which is formed by bending an extension from the edge of the hung zone 312 towards the central axis 2.

Third Embodiment

A difference between the left atrial appendage occluder 200 of the first embodiment and a left atrial appendage occluder 400 according to a third embodiment is that a fixing part 410 of the left atrial appendage occluder 400 converges at an end portion and is connected with a connection part 430, and the fixing part 410 comprises a proximal end surface zone 411 formed by radially spreading from this end portion, and a hung zone 412 formed by the extension from the proximal end surface zone 411 to the distal end after bending, wherein an opening 3 is defined by the hung zone 412 towards the distal end. The fixing part 410 may be integrally braided with braid wires. For example, the proximal end surface zone 411 and the hung zone 412 are braided bodies having a plurality of grids. The fixing part 410 may also be formed by cutting a metal tube. For example, the proximal end surface zone 411 and the hung zone 412 respectively comprise a plurality of cut metal rod parts connected with or spaced apart from one another. According to requirements or demands, such as those for making the deformation capacity of the fixing part smaller than that of the sealing part, those with ordinary skill in the art may choose suitable braid wires or metal tubes, such as nickel-titanium alloy; and furthermore, the wire diameters of braid wires, braiding methods, and so on, or the tube diameters, thicknesses of tube walls, cutting widths, and so on, of suitable metal tubes may be further chosen, which will not be described in detail herein. The structure of the fixing part 420 may be the same as the structure of the sealing part 220 of the first embodiment, and will not be repeated herein.

Figure 5:
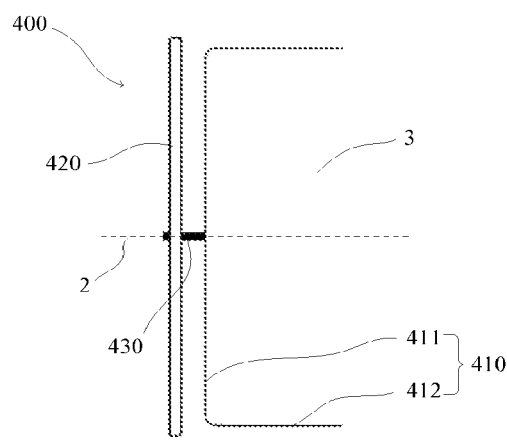
FIG. 5 is a structural schematic diagram of an exemplary left atrial appendage occluder according to a third embodiment of the present disclosure.
Figure 6:
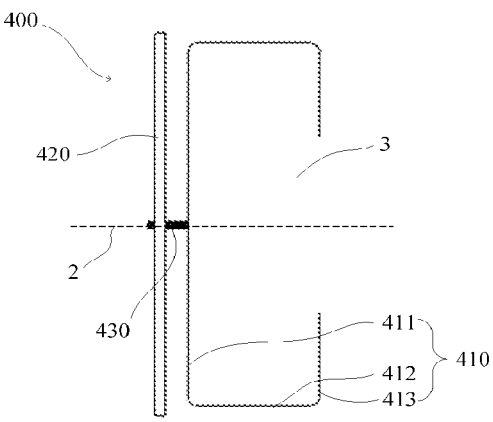
FIG. 6 is a structural schematic diagram of another exemplary left atrial appendage occluder according to the third embodiment of the present disclosure.

Applying the definitions used for the first embodiment, the fixing part 410 in the third embodiment may be defined to be a fully opened opening 3 or a partially opened opening 3. For example FIG. 5 illustrates the fixing part 410 with a fully opened opening 3, and FIG. 6 illustrates the fixing part 410 with a partially opened opening 3. The opening 3 is partially blocked by an edge zone 413 which is formed by bending an extension from the edge of the hung zone 412 to the central axis 2.

Fourth Embodiment

Figure 7:
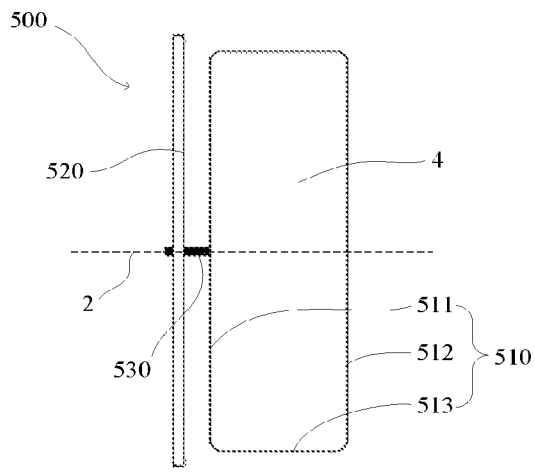
FIG. 7 is a structural schematic diagram of an exemplary left atrial appendage occluder according to a fourth embodiment of the present disclosure.
Figure 8:
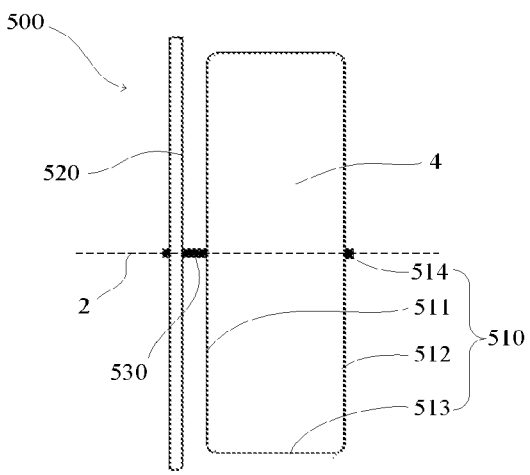
FIG. 8 is a structural schematic diagram of another exemplary left atrial appendage occluder according to the fourth embodiment of the present disclosure.

A difference between the left atrial appendage occluder 200 in the first embodiment and a left atrial appendage occluder 500 according to a fourth embodiment is that a fixing part 510 of the left atrial appendage occluder 500 comprises a proximal end surface zone 511, a distal end surface zone 512, and a cylindrical surface zone 513 for connecting the proximal end surface zone 511 and the distal end surface zone 512, wherein a cavity 4 is cooperatively defined by the proximal end surface zone 511, the distal end surface zone 512 and the cylindrical surface zone 513. A connection part 530 is connected with the proximal end surface zone 511. For example FIGS. 7 and 8 illustrate the respective approximately cylindrical fixing parts 510, and the difference therebetween simply lies in the fact that the fixing part 510 in FIG. 8 further comprises a distal end portion 514, and the distal end surface zone 512 converges at the distal end portion 514.

The fixing part 510 may be integrally braided with braid wires or be formed by cutting of metal tubes. For example (see FIG. 8), if the fixing part 510 is integrally braided with braid wires, all of the braid wires converge at the distal end portion 514 and are fixed to be prevented from being dispersed; and if the fixing part 510 is formed by cutting of metal tubes, all of the cutting units converge at the distal end portion 514. According to requirements or demands, such as those for making the deformation capacity of the fixing part smaller than that of the sealing part, those with ordinary skill in the art may choose suitable braid wires or metal tubes, such as nickel-titanium alloy; and furthermore, the wire diameters of braid wires, braiding methods, and so on, or the tube diameters, thicknesses of tube walls, cutting widths, and so on, of suitable metal tubes may be further chosen, which will not be described in detail herein. The structure of a sealing part 520 may be the same as the structure of the sealing part 220 of the first embodiment, and will not be repeated herein.

Fifth Embodiment

Figure 9:
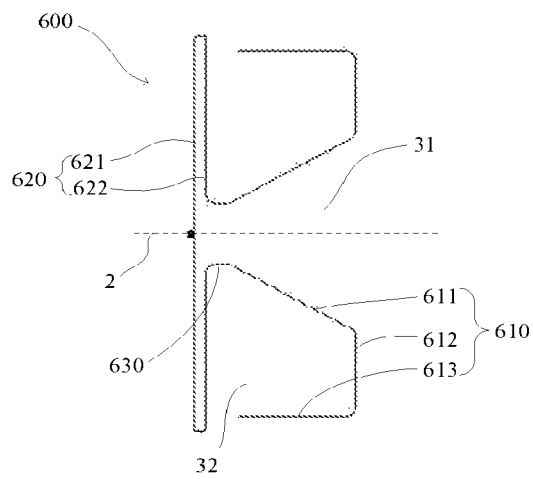
FIG. 9 is a structural schematic diagram of an exemplary left atrial appendage occluder according to a fifth embodiment of the present disclosure.
Figure 10:
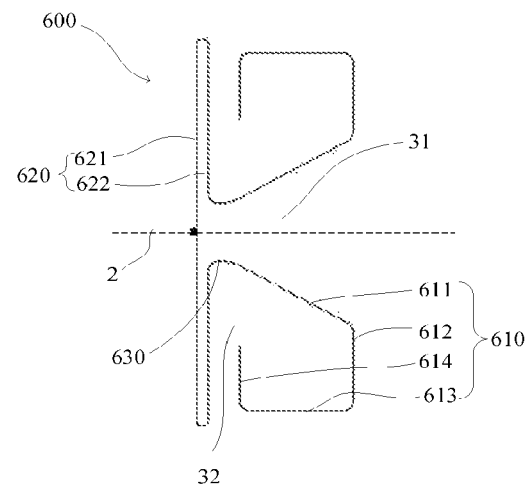
FIG. 10 is a structural schematic diagram of another exemplary left atrial appendage occluder according to the fifth embodiment of the present disclosure.

Referring to FIGS. 9 and 10 together, a sealing part 620 of a left atrial appendage occluder 600 in accordance with a fifth embodiment of the present disclosure is a dual-layer disc. The dual-layer disc comprises a proximal end disc surface 621 and a distal end disc surface 622, wherein a first opening 31 is defined in the distal end disc surface 622, with the first opening being defined at the center of the distal end disc surface 622. A connection part 630 is connected with the distal end disc surface 622 at the first opening 31, meanwhile the first opening 31 is kept open. The connection part 630 may be integrally formed with the sealing part 620.

An end portion of the fixing part 610 is connected with the connection part 630, and meanwhile the first opening 31 is kept open. The fixing part 610 comprises a concave zone 611 formed by radially spreading from the end portion to the distal end, and a hung zone 613 formed by the extension from the concave zone 611 to the proximal end after bending. A second opening 32 is defined by the hung zone 613 towards the proximal end. The fixing part 610 may further comprise a distal end surface zone 612 connecting the hung zone 613 with the concave zone 611. The fixing part 610 may be integrally formed with the connection part 630.

The sealing part 620 may be a braided dual-layer disc or a cut dual-layer disc. The connection part 630 may be selected to be of any suitable structure. The fixing part 610 may be integrally braided with braid wires. For example, the concave zone 611 and the hung zone 613 are braided bodies having a plurality of grids. The fixing part 610 may be also formed by cutting of metal tubes. For example, the concave zone 611 and the hung zone 613 respectively comprise a plurality of cut metal rod parts that may be connected with or spaced apart from one another. According to requirements or demands, such as those for making the deformation capacity of the fixing part smaller than that of the sealing part, those of ordinary skill in the art may choose suitable braid wires or metal tubes, such as nickel-titanium alloy; and furthermore, the wire diameters of braid wires, braiding methods, and so on, or the tube diameters, thicknesses of tube walls, cutting widths, and so on, of suitable metal tubes may be further chosen, which will not be described in greater detail herein. In addition, the sealing part 620, the connection part 630 and the fixing part 610 may be integrally formed, for example, by integral braiding or integral cutting.

Applying the definitions used for the first embodiment, the fixing part 610 in this embodiment may have a fully opened opening 32 or a partially opened opening 32. For example FIG. 9 illustrates the fixing part 610 with a second fully opened opening 320, and FIG. 10 illustrates the fixing part 610 with a second partially open opening 310. The second opening 32 is partially blocked by an edge zone 614 which is formed by bending an extension from the edge of the hung zone 613 to a central axis 2.

Sixth Embodiment

Referring to FIG. 11, a difference from the left atrial appendage occluder 200 in the first embodiment is that a sealing part 720 of a left atrial appendage occluder 700 in a sixth embodiment of the present disclosure is a single-layer disc, the single-layer disc being a braided single-layer disc or a cut single-layer disc. For example, referring to FIG. 12, the sealing part 720 may specifically comprise a sealing disc surface 721 and a fixed connecting part 722 located near the center of the sealing disc surface 721. A central axis 2 extends through the fixed connecting part 722, and a connection part 730 is connected with the fixed connecting part 722. The fixed connecting part 722 is used for connecting with an external delivery system. If the sealing part 720 is a braided single-layer disc, all the braid wires converge to the fixed connecting part 722; and if the sealing part 720 is a cut single-layer disc, all cut rod parts converge to the fixed connection part 722. Further, the single-layer disc may be covered with a PET or PTFE film to improve the sealing effect.

The connection part 730 and the fixing part 710 of the sixth embodiment may be the same as those in the first embodiment. Of course, other suitable structures may be also adopted as long as a deformation capacity of the sealing part 720 is greater than that of the fixing part 710. For example, the fixing part 710 of this embodiment may be any one of the fixing part structures in the second, third, fourth, or fifth embodiments, or other structures based on the teachings of the present disclosure.

Seventh Embodiment

Referring to FIG. 13, a left atrial appendage occluder of a seventh embodiment is based on the left atrial appendage occluder in the first embodiment, and it is further defined that a connection part 230A is elastic and may be pulled, compressed and/or bent under the effects of a fixing part and/or a sealing part. The elastic connection part 230A may be a braided body or a cut body, or other various applicable structures, which will not be described herein. For example, FIG. 13 illustrates a spring-shaped connection part 230A. Of course, the elastic connection part 230A may be similarly applied to any one of the left atrial appendage occluders in the second, third, fourth, fifth or sixth embodiments, or other left atrial appendage occluders based on the teachings of the present disclosure.

Whatever specific structures are provided for the sealing part, the fixing part and the connection part, the left atrial appendage occluders of the several embodiments described above meet the requirements that the axial deformation capacity of the sealing part is greater than that of the fixing part, and/or the radial deformation capacity of the sealing part is greater than that of the fixing part. Of course, the left atrial appendage occluders meeting the requirement that the deformation capacity of the sealing part is greater than that of the fixing part are not limited to the above embodiments. Therefore, the above embodiments are not limitations to the present disclosure, and any suitable left atrial appendage occluder meeting the requirement should be within the scope of the present disclosure, and those with ordinary skill in the art may select or design various suitable left atrial appendage occluder structures based on the teachings of the present disclosure.

The conclusion that the deformation capacity of a sealing part is greater than that of a fixing part can be understood as meaning that, under the same radial force, the radial length variation of the sealing part is greater than that of the fixing part, or the radial length variation ratio of the sealing part is greater than that of the fixing part; or can be understood as also meaning that under the same radial force, the displacement of the sealing part along the direction of the axial force is greater than that of the fixing part.

As seen from the above, there are various testing methods or representation methods for the deformation capacity of the sealing part and that of the fixing part. Some of the methods will be demonstrated in the following examples. It should be understood that the following various testing methods or representation methods for the deformation capacity are equivalent to each other, so that the conclusion that the deformation capacity of the sealing part is greater than that of the fixing part obtained by adopting any one of the testing methods or representation methods can satisfy the proposal of the present disclosure that the deformation capacity of the sealing part is greater than that of the fixing part.

First Exemplary of Deformation Capacity Testing Method

In the present testing method, the radial deformation capacity of a part (the fixing part or the sealing part) may be represented by testing the radial length variation of the part under the action of the same radial force. For example, the radial deformation capacities of the fixing part and the sealing part are respectively tested by measuring the radial length variations thereof under the action of the same radial force, resulting in that the left atrial appendage occluder meets the requirement that the radial length variation of the fixing part is less than that of the sealing part. Alternatively, the radial deformation capacities of the fixing part and the sealing part are respectively tested by measuring the radial length variation ratios thereof, resulting in that the left atrial appendage occluder meets the requirement that the radial length variation ratio of the fixing part is less than that of the sealing part. This first exemplary of a deformation capacity testing method will be described as below aiming at one or more specific left atrial appendage occluder structures illustrated in the above embodiments.

In the specific implementations of the first exemplary testing method, a plate method may be adopted to test the radial length variations of the fixing part and the sealing part respectively under the same radial force. For example, referring to FIGS. 14 and 15, the plate method may be adopted to test the left atrial appendage occluder 200 of the first embodiment.

Referring to FIG. 14, first, a radial force F is applied onto the fixing part 210 via two parallel plates 61 and 62 while the sealing part 220 is freely maintained in an expanded state. Specifically, the parallel plates 61 and 62 are oppositely placed on a diameter of the fixing part 210 and respectively applied with equal and opposite radial forces F; the diameter of the fixing part 210 passes through the central axis 2 and is perpendicular to the central axis 2. During the whole testing process, the two parallel plates 61 and 62 are maintained in parallel with each other, i.e., the two parallel plates 61 and 62 are maintained in parallel with the central axis 2 throughout the testing process. Any one of the plates covers at least the maximum radial contour of the fixing part 210, preferably covers the entire fixing part 210 in a direction in parallel with the central axis 2; and herein, the maximum radial contour of the fixing part 210 is in the hung zone, the whole hung zone being covered with both the two plates during the testing process. If the diameter of the fixing part 210 with plates in a naturally expanded state is R1, the radial length variation of the fixing part 210 under the radial force F is ΔR1, which represents the diameter D-value between the diameter before and after radial compression, and the radial length variation ratio is represented by ΔR1/R1. In order to avoid self deformation of the plates during the radial force applying process, the thickness of each plate is at least 5 mm, so that the radial force may be uniformly applied everywhere on the plate.

Referring to FIG. 15, the sealing part 220 is tested by the same plate method as above, that is, under the same radial forces F which are equal and opposite and which are applied for the same amount of time. The radial length variation ΔR2 or the radial length variation ratio ΔR2/R2 of the sealing part 220 is tested while the fixing part 210 is in a naturally expanded state, and at this moment, the maximum radial contour of the sealing part 220 is on the disc edge of the dual-layer disc. According to the testing conditions above, under the same radial force, the radial length variation ΔR2 of the sealing part 220 of the left atrial appendage occluder 200 according to the embodiments of the present disclosure is greater than the radial length variation ΔR1 of the fixing part 210; or, the radial length variation ratio ΔR2/R2 of the sealing part 220 of the left atrial appendage occluder 200 according to the embodiments of the present disclosure is greater than the radial length variation ratio ΔR1/R1 of the fixing part 210.

Figure 16:
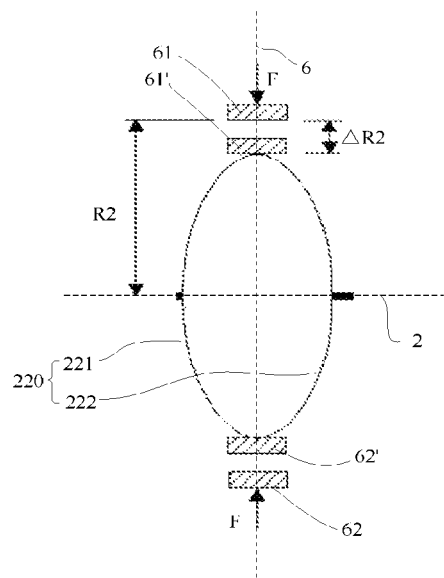
Figure 17:
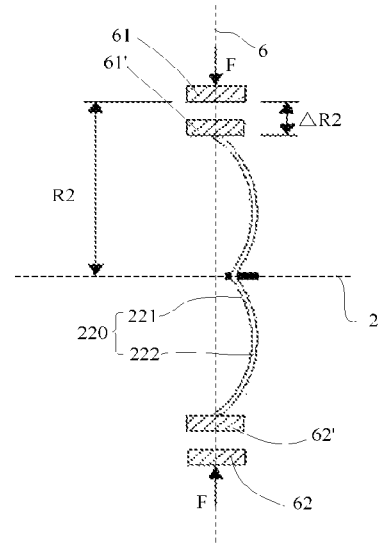
Figure 18:
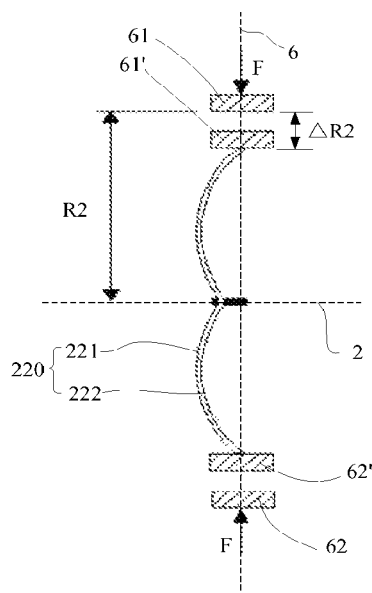

Due to the dual-layer disc structure of the sealing part 220 (e.g. comprising the proximal end disc surface 221 and the distal end disc surface 222), the sealing part 220 may be subject to various deformations under a radial force. For example, referring to FIG. 16, when the two plates under the action of a radical force respectively move from plate location 61 and 62 along a diameter 6 to 61' and 62', the proximal end disc surface 221 and the distal end disc surface 222 deform towards opposite directions. As shown in FIG. 16, the proximal end disc surface 221 deforms and protrudes towards the proximal end, the distal end disc surface 222 deforms and protrudes towards the distal end, and then the radial displacement (along the direction of the diameter 6) of the plates is tested as the radial length variation of the sealing part 220. For another example, referring to FIGS. 17 and 18, when the two plates under the action of a radical force respectively move from plate locations 61 and 62 to 61' and 62', the proximal end disc surface 221 and the distal end disc surface 222 may deform towards the same direction, and the two disc surfaces as shown in FIG. 17 deform and protrude towards the distal end, and the two disc surfaces as shown in FIG. 18 deform and protrude towards the proximal end, and then the radial displacement of the plates is tested as the radial length variation of the sealing part 220.

The fixing part of the left atrial appendage occluder in the second embodiment also comprises an opening facing to the proximal end, and the maximum radial contour of the fixing part is in the hung zone thereof. As measured with the same plate method, under the same action of a radial force, the radial length variation ΔR2 of the sealing part of the left atrial appendage occluder is greater than the radial length variation ΔR1 of the fixing part, or the radial length variation ratio ΔR2/R2 of the sealing part of the left atrial appendage occluder according to the second embodiment of the present disclosure is greater than the radial length variation ratio ΔR1/R1 of the fixing part. It should be understood that the structure of the sealing part of the left atrial appendage occluder in the second embodiment is the same as the structure of the sealing part in the first embodiment, so measurement of the sealing part will not be repeated.

The fixing part of the left atrial appendage occluder in the third embodiment also comprises an opening facing to the distal end, and the maximum radial contour of the fixing part is in the hung zone. As measured by the same plate method, under the same action of a radial force, the radial length variation ΔR2 of the sealing part of the left atrial appendage occluder is greater than the radial length variation ΔR1 of the fixing part, or the radial length variation ratio ΔR2/R2 of the sealing part of the left atrial appendage occluder according to the third embodiment of the present disclosure is greater than the radial length variation ratio ΔR1/R1 of the fixing part. It should be understood that the structure of the sealing part of the left atrial appendage occluder in the third embodiment is the same as the structure of the sealing part in the first embodiment, so measurement of the sealing part will not be repeated.

Figure 19:
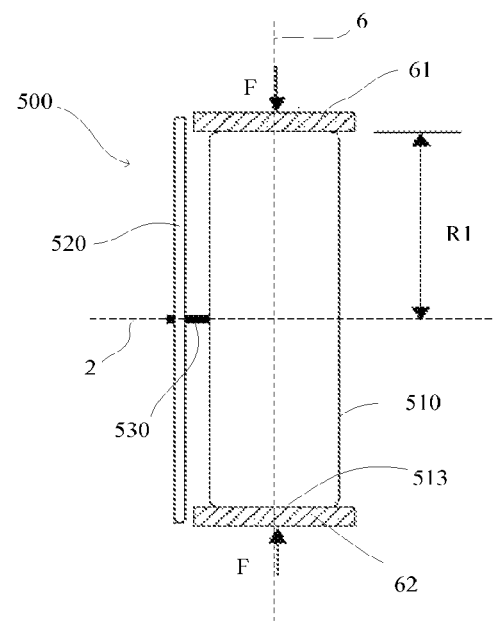
FIG. 19 is a schematic diagram for testing the left atrial appendage occluder of the fourth embodiment by using the first exemplary testing method.

Referring to FIG. 19, the fixing part 510 of the left atrial appendage occluder 500 of the fourth embodiment comprises a closed dual-layer disc, and the maximum radial contour of the fixing part 510 is in the cylindrical surface zone 513, so that two plates may cover the entire cylindrical surface zone 513. As measured by the same plate method, under the same action of a radical force, the radial length variation ΔR2 of the sealing part of the left atrial appendage occluder is greater than the radial length variation ΔR1 of the fixing part, or the radial length variation ratio ΔR2/R2 of the sealing part of the left atrial appendage occluder according to the fourth embodiment of the present disclosure is greater than the radial length variation ratio ΔR1/R1 of the fixing part. It should be understood that the structure of the sealing part 520 of the left atrial appendage occluder 500 in the fourth embodiment is the same as the structure of the sealing part 220 in the first embodiment, so that the measurement of the sealing part 520 will not be repeated.

Figure 20:
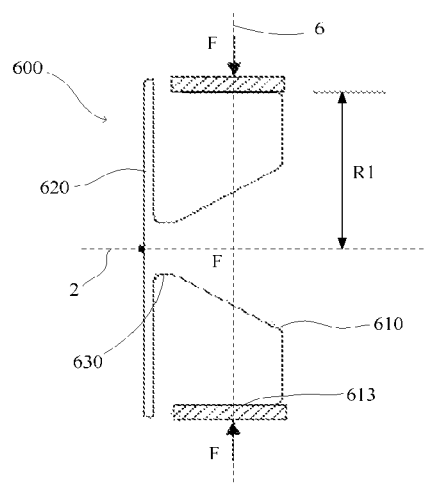
FIGS. 20 and 21 are schematic diagrams for testing the left atrial appendage occluder of the fifth embodiment by using the first exemplary testing method.
Figure 21:
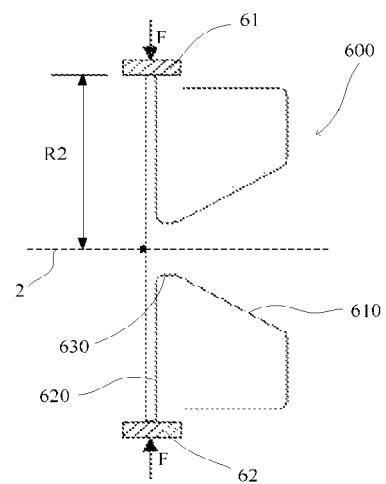
Figure 22:
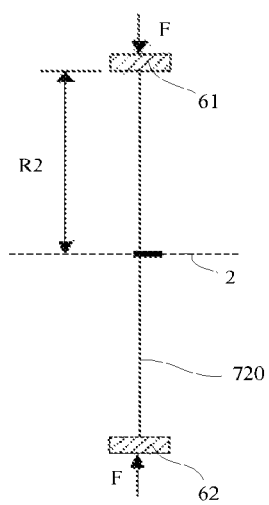
FIG. 22 is a schematic diagram for testing the left atrial appendage occluder of the sixth embodiment by using the first exemplary testing method.

The fixing part 610 of the left atrial appendage occluder 600 of the fifth embodiment also comprises a second opening facing to the proximal end, and the maximum radial contour of the fixing part 610 is in the hung zone, as shown in FIG. 20. The sealing part 620 is a dual-layer disc, and the maximum radial contour thereof is still positioned at the edge of the disc surface of the dual-layer disc, as shown in FIG. 21. As measured by the same plate method of the left atrial appendage occluder of the first embodiment, under the same action of a radial force, the radial length variation ΔR2 of the sealing part of the left atrial appendage occluder is greater than the radial length variation ΔR1 of the fixing part or the radial length variation ratio ΔR2/R2 of the sealing part of the left atrial appendage occluder is greater than the radial length variation ratio ΔR1/R1 of the fixing part.

The structure of the fixing part of the left atrial appendage occluder in the sixth embodiment is the same as that of any one of the left atrial appendage occluders in the first to fifth embodiments, so that the measurement of the fixing parts will not be repeated herein. The sealing part 720 in the sixth embodiment is a single-layer disc, the maximum radial contour thereof is at the radial edge of the disc surface, and similar to the dual-layer disc, two plates 61 and 62 may be placed at the radial edge of the disc surface for implementing the plate test. Under the same action of a radial force, the radial length variation ΔRZ of the sealing part 720 of the left atrial appendage occluder is greater than the radial length variation ΔR12 of the fixing part or the radial length variation ratio ΔR2/R2 of the sealing part of the left atrial appendage occluder according to the sixth embodiment is greater than the radial length variation ratio ΔR1/R1 of the fixing part.

Figure 23:
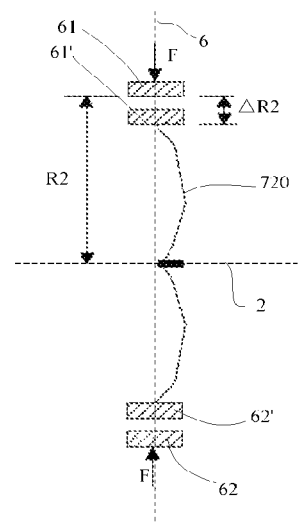
FIGS. 23 and 24 are schematic diagrams for testing a liable deformation structure of a sealing part of the sixth embodiment by using the first exemplary testing method.
Figure 24:
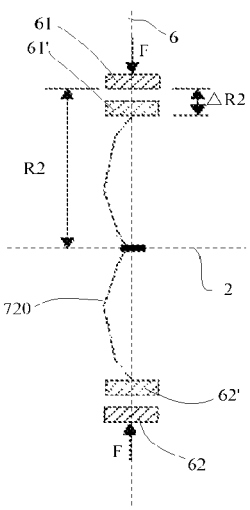

Similarly, when the two plates 61 and 62 radially compress the single-layer disc respectively, the disc surface of the single-layer disc may protrude from the radial direction 6 and deform towards the distal end, referring to FIG. 23, or the single-layer disc may also protrude from the radial direction 6 and deform towards the proximal end, as shown in FIG. 24, and then the radial displacement of the plate 61 or 62 may be tested as the radial length variation of the sealing part. As measured under the same action of a radial force, the radial length variation ΔR2 of the sealing part of the left atrial appendage occluder is greater than the radial length variation ΔR1 of the fixing part or the radial length variation ratio ΔR2/R2 of the sealing part of the left atrial appendage occluder according to the sixth embodiment is greater than the radial length variation ΔR1/R1 of the fixing part.

Figure 25:
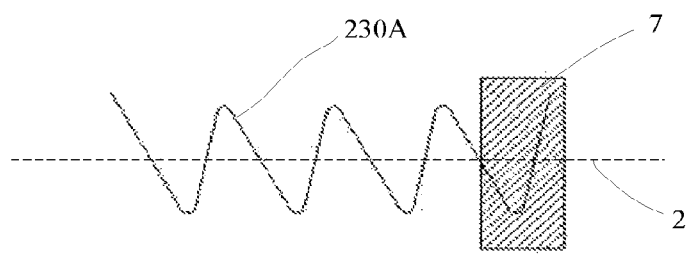
FIG. 25 is a schematic diagram for testing the left atrial appendage occluder of the seventh embodiment by using the first exemplary testing method.

Similarly, the left atrial appendage occluder in the seventh embodiment may also be tested by the plate method. In order to avoid deformation of the elastic connection part 230A caused by adapting to the radial compression of the fixing part or the sealing part in the radial compression process of the plates, as shown in FIG. 25, in the process of measurement, a clamping component 7 is used for fixing one end portion of the connection part 230A. For example, when the fixing part is compressed, the end portion, which is adjoined tightly to the fixing part, of the connection part 230A is clamped, and when the sealing part is compressed, the end portion, which is adjoined tightly to the sealing part, of the connection part 230A is clamped. The plate test method of the fixing part and the sealing part is basically the same as any of the above-mentioned methods, and will not be repeated herein.

Figure 26:
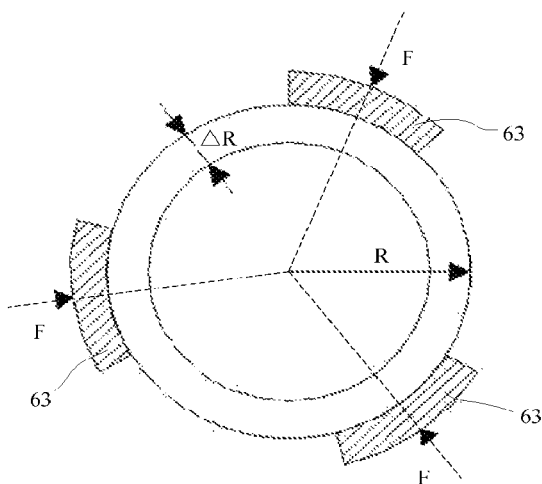
FIG. 26 is a schematic diagram of another specific testing structure of the first exemplary testing method.

The above plate test method is only an exemplary test method and is not intended to limit the present disclosure. Those with ordinary skill in the art can use any suitable method equivalent to the plate test method to perform the test. For example, in another specific implementation of the first test method, the radial force may also be applied uniformly onto the periphery of a part to be tested to carry out the test. Specifically, referring to FIG. 26, three curved plates 63 may be evenly disposed on the maximum radial contour of the part to be tested (the fixing part or the sealing part) upwardly in the same circumferential direction, a radial force F along radial direction on said curved plates 63 is applied during the test, and the variation or variation ratio of the radial length R of the part is tested. Similarly, in order to achieve a uniform radial force application, the thickness of each curved plate may be set as at least 5 mm. In addition, a radial force tester (No. RX550-100) of Machine Solution Inc (MSI) may also be used for testing the left atrial appendage occluder.

After a left atrial appendage occluder is implanted in a human body, inappropriate choice of implantation location may occur. For example, the fixing part may be implanted too deeply into the cavity of the left atrial appendage, resulting in an axial length of the naturally expanded occluder being less than a relative distance between the implanted fixing part and sealing part, thereby causing a mutual pulling action between the fixing and sealing parts. Alternatively, after implantation, the occluder moves along with the heart. Due to the difference of movement magnitude or direction in various locations, the mutual pulling action may also occur between the fixing part and the sealing part. Generally, mutual pulling between the fixing and sealing parts is carried out by a connection part. When the fixing part is pulled by the sealing part, as the fixing part is fixed to the cavity of the left atrial appendage by a radial support force around a peripheral zone of the central axis 2, and therefore, the fixing part is mainly attached closely to the peripheral zone of the cavity of the left atrial appendage to resist such pulling action. Hence, axial pulling to the fixing part will cause its radial deformation. If the pulling action is large enough, it might cause the fixing part to separate from the cavity wall of the left atrial appendage and then fall off from the left atrial appendage occluder, resulting in implantation failure. When the sealing part is pulled by the fixing part, as the sealing part is of a disc surface structure, and is connected to the connection part on the disc surface, the axial pulling to the sealing part will cause similar radial deformation.

Thus, when the fixing part and the sealing part are pulled towards each other, one part which easily tends to deform radially will be pulled dominantly by the other one. For example, under the same action of a radial force, the radial length variation of the fixing part in accordance with this embodiment of the present disclosure is less than the radial length variation of the sealing part, or the radial length variation ratio of the fixing part in accordance with this embodiment of the present disclosure is less than the radial length variation ratio of the sealing part. Then, the fixing part will pull the sealing part dominantly in the mutual pulling process, thereby causing the deformation of the sealing part towards the fixing part (or toward the distal end). This deformation causes the sealing part to be attached more closely to the left atrial wall at the opening of the left atrial appendage as compared to the naturally expanded state, thereby enhancing the sealing effect of the sealing part to the opening of the left atrial appendage, avoiding the formation of a gap between the sealing part and the left atrial wall, thereby further preventing blood from flowing into the cavity of the left atrial appendage and preventing thrombi from flowing into the left atrium through the gap to cause a stroke or systemic embolism. Meanwhile, the fixing part dominating the pulling is not easily pulled away from the cavity wall of the left atrial appendage by the sealing part. Therefore, the occluder is more firmly fixed in the left atrial appendage, preventing the occluder from being disengaged from the left atrial appendage.

Second Exemplary of Deformation Capacity Testing Method

In this testing method, the axial deformation capacity of a part may be obtained by testing the axial (along the central axis 2) displacement of the part under the same action of an axial force while a certain part of the part to be tested (the fixing part or the sealing part) is constrained. The constraint is of an equal size constraint, i.e., no elastic deformation occurs during the constraining process, or the elastic deformation is slight, even substantially negligible. Further, it was selected to apply an axial force at the location where no elastic deformation will occur. For example, the same axial force may be applied respectively to one end portion, which is connected to the connection part, of the part to be tested. The axial displacement of the part to be tested is tested to represent the respective deformation capacity. The axial displacement of the part is the axial displacement at a point of force exertion. The left atrial appendage occluder meets the requirement where the axial displacement of the fixing part is less than the axial displacement of the sealing part. A second exemplary deformation capacity testing method will be described in detail below aiming at one or more specific left atrial appendage occluders as shown in all embodiments shown above.

The second exemplary deformation capacity testing method may be adopted to test the left atrial appendage occluder of the first embodiment, in which the fixing part and the sealing part are independently tested. For example, only an individual fixing part or an individual sealing part is tested each time.

Referring to FIG. 27, in the process of testing the fixing part 210, an annular clamping component 71 is used to clamp the fixing part 210 at the maximum radial contour in the circumferential direction. The annular clamping component 71 surrounds the central axis 2 and is perpendicular to the central axis 2, and the maximum radial contour of the fixing part 210 is in a hung zone 212. In the clamping process, the radial size of the clamped position of the fixing part 210 basically maintains the size in a naturally expanded state, and the elastic deformation may be basically ignored. At the end portion 214, which is connected with the connection part, of the fixing part 210, an axial force F1 is applied along the central axis 2 and towards the direction of the sealing part 220, and this end portion 214 may not generate elastic deformation while the axial force F1 is applied. The axial displacement $\Delta O1$ of a projection O1 of the end portion 214 on the central axis 2 along with the F1 is measured, and the $\Delta O1$ represents the deformation (or the deformation capacity) of the fixing part 210 in the second testing method; and in the whole loading process of the axial force F1, the self-clamping state of the clamping component 71 is kept unchanged.

It can be seen from the above, after the left atrial appendage occluder is implanted into a human body, under the condition that part of the fixing part is clamped, such as the fixing part 210 clamped at the maximum contour in the first embodiment, the axial displacement measured under the action of an axial pulling force shows the axial deformation capacity of the fixing part pulled by the sealing part with the constraint of the cavity of the left atrial appendage, after the fixing part has been implanted into the cavity of the left atrial appendage. Pulled by the same axial force, the larger the $\Delta O1$ is, the more easily the fixing part tends to deform.

Referring to FIG. 28, the sealing part 220 in the first embodiment comprises a proximal end disc surface 221, a distal end disc surface 222, a proximal end tip 223 positioned on the proximal end disc surface 221, and a distal end tip 224 positioned on the distal end disc surface 222, wherein the connection part is connected with the distal end tip 224. In the process of testing the sealing part 220, a clamping component 72 is used to directly clamp the sealing part 220 at the distal end tip 224. At the proximal end tip 223 of the sealing part 220, an axial force F1 is applied along the central axis 2 and away from the fixing part 210, the axial force being identical with the axial force in the process of testing the fixing part 210; and the axial displacement $\Delta O2$ of the projection O2 of the proximal end tip 223 on the central axis 2 along with the force F1 is measured, and $\Delta O2$ represents the axial deformation (or the deformation capacity) of the sealing part 220 in the second testing method.

It can be seen from the above, after the left atrial appendage occluder is implanted into a human body, under the condition that part of the sealing part is clamped, such as the sealing part 220 clamped at the distal end tip 224 in the first embodiment, the axial displacement with the application of an axial pulling force F1 shows the axial deformation capacity of the sealing part 220 pulled by the fixing part 210 with the constraint of the tissue wall of the opening of the left atrial appendage, after the sealing part 220 is implanted into the cavity of the left atrial appendage. Pulled by the same axial force, the larger the $\Delta O2$ is, the more easily the sealing part 220 tends to deform.

As can be measured from the second exemplary deformation capacity testing method, under the same action of an axial force, the axial displacement $\Delta O1$ of the fixing part is less than the axial displacement $\Delta O2$ of the sealing part. It can be understood that when the fixing part and the sealing part are pulled towards each other, one part with the greater axial displacement is pulled dominantly by the other part. For example, under the same action of an axial force, the axial displacement of the fixing part according to the embodiment of the present disclosure is less than that of the sealing part. In the process that the fixing part and the sealing part are pulled towards each other, the fixing part dominantly pulls the sealing part, so that the sealing part deforms towards the fixing part (or towards the distal end). Such deformation makes the sealing part more tightly pressed to the wall of the left atrium at the opening of the left atrial appendage compared with a naturally expanded state, thereby improving the sealing effect of the sealing part on the opening of the left atrial appendage, and avoiding the formation of a gap between the sealing part and the wall of the left atrium, thereby preventing blood from flowing into the cavity of the left atrial appendage and preventing thrombi from flowing into the left atrium through the gap. Meanwhile, the fixing part dominating the pulling is not easily pulled away from the cavity wall of the left atrial appendage by the sealing part. Therefore, the occluder is more firmly fixed in the left atrial appendage, preventing the occluder from being disengaged from the left atrial appendage.

Similarly, the second exemplary deformation capacity testing method may be used to test the left atrial appendage occluder in other embodiments. For example, the fixing part of the left atrial appendage occluder in the second embodiment also comprises an opening facing to the proximal end, and the maximum radial contour of the fixing part is in the hung zone. Therefore, at the maximum radial contour of the fixing part, an annular clamping component may also be used to clamp the fixing part. It can be measured from the same second exemplary deformation capacity testing method that, under the same action of an axial force, the axial displacement $\Delta O1$ of the fixing part of the left atrial appendage occluder is less than the axial displacement $\Delta O2$ of the sealing part. It should be understood that the structure of the sealing part of the left atrial appendage occluder in the second embodiment is the same as that of the sealing part of the left atrial appendage occluder in the first embodiment, so that the test process of the sealing part will not be repeated.

The fixing part of the left atrial appendage occluder in the third embodiment comprises an opening facing to the distal end, and the maximum radial contour of the fixing part is in the hung zone. Therefore, at the maximum radial contour of the hung zone, an annular clamping component may also be used to clamp the fixing part. It can be measured with the same second exemplary deformation capacity testing method that, under the same action of an axial force, the axial displacement $\Delta O1$ of the fixing part of the left atrial appendage occluder is less than the axial displacement $\Delta O2$ of the sealing part. It should be understood that the structure of the sealing part of the left atrial appendage occluder in the third embodiment is the same as that of the sealing part of the left atrial appendage occluder in the first embodiment, so that the testing process of the sealing part will not be repeated.

The fixing part of the left atrial appendage occluder in the fourth embodiment (such as the left atrial appendage occluder in FIG. 7 or 8) comprises a closed two-layer disc, and the maximum radial contour of the fixing part is in a cylindrical surface zone thereof. Therefore, at the maximum radial contour of the cylindrical surface zone, an annular clamping component may be used to clamp the fixing part. It can be measured by the same second exemplary deformation capacity testing method that, under the same action of an axial force, the axial displacement $\Delta O1$ of the fixing part of the left atrial appendage occluder is less than the axial displacement $\Delta O2$ of the sealing part. It should be understood that the structure of the sealing part of the left atrial appendage occluder in the fourth embodiment is the same as that of the sealing part of the left atrial appendage occluder in the first embodiment, and therefore the testing process of the sealing part will not be repeated.

The fixing part 510 of the left atrial appendage occluder 500 shown in FIG. 8 further includes a distal end portion 514 (see FIG. 29). In the case of testing the fixing part by adopting the second exemplary deformation capability testing method, a clamping component 73 also can be adopted at this distal end portion 514 to clamp the fixing part 510 instead of clamping the fixing part at the maximum radial contour; and subsequently, applying the axial force F1, the axial displacement $\Delta O1$ of the fixing part 510 is tested while the other steps in the testing method are the same.

The left atrial appendage occluder 500 in the fifth embodiment is typically formed integrally, for example, by integral braiding or integral cutting. Therefore, it is impossible to divide it in a testing process; for example, when the fixing part 610 is tested, it is impossible to independently separate the sealing part 620 therefrom, and vice versa. Therefore the testing method for the occluder 500 in the fifth embodiment is slightly different from the testing method for the occluder in the first to fourth embodiments, but the testing principles are identical.

Referring to FIG. 30, in the process of testing the fixing part 610, the annular clamping component 71 is adopted to clamp the fixing part 610 at the maximum radial contour of the fixing part 610 along the circumferential direction. The annular clamping component surrounds the central axis 2 and is perpendicular to the central axis 2, and the maximum radial contour of the fixing part 610 is in the hung zone thereof. Meanwhile, another annular clamping component 74 is adopted at the connection part 630 to clamp the connection part 630, and in the clamping process the radial size of the connection part 630 is basically unchanged and elastic deformation thereof can be substantially ignored. The axial force F1 is applied to the annular clamping component 74 along the central axis 2 and away from the fixing part 610. The axial displacement $\Delta O1$ of a projection O1, of a position where the axial force F1 is applied on the clamping component 74, on the central axis 2 along with F1 is measured. This $\Delta O1$ is adopted to represent the deformation (or deformation capacity) of the fixing part 610 in the second testing method.

Referring to FIG. 31, in the process of testing the sealing part 620, the other annular clamping component 74 can be used to clamp the connection part 630. The same axial force F1 is applied along the central axis 2 and away from the fixing part 610, and the axial displacement $\Delta O2$ of a projection O1, of a position where the axial force F1 is applied, onto the proximal end disc surface 621, on the central axis 2 along with F1 is measured. The $\Delta O2$ is used to represent the deformation (or deformation capacity) of the sealing part 620 in the second testing method. It may be measured that, under the same action of an axial force F1, the axial displacement $\Delta O1$ of the fixing part 610 of the left atrial appendage occluder 600 is less than the axial displacement $\Delta O2$ of the sealing part 620.

The structure of the fixing part of the left atrial appendage occluder in the sixth embodiment is the same as the structure of the fixing part in the first to fifth embodiments, and the testing process of the fixing part will not be described here. Referring to FIG. 12, the sealing part in the sixth embodiment is a single-layer disc, comprising, for instance, a sealing disc surface and a fixed connecting part through which the central axis 2 extends, thus rendering it impossible to test with the same testing method as the dual-layer disc. Referring to FIG. 32, the maximum radial contour of the sealing part 720 is at the radial edge of the disc surface 721, and in the same circumferential direction of this maximum radial contour, an annular clamping component 75 is adopted to constrain this sealing part 720. Similarly, the elastic deformation of the single-layer disc can be ignored in the clamping process. In the case of maintaining said clamping state, the axial force F1 is applied along the central axis 2 and away from the fixing part from the fixed connecting part, and the displacement $\Delta O2$ of the fixed connecting part 722 along the central axis 2 is measured.

When the same axial force F1 is adopted to test the axial displacement of the fixing part, it is measured that the axial displacement ΔO1 of the fixing part of the left atrial appendage occluder is less than the axial displacement ΔO2 of the sealing part.

When the second exemplary deformation capacity testing method is used to test the left atrial appendage occluder, each of the fixing part and the sealing part is tested individually. For example, only an individual fixing part or an individual sealing part is tested each time without considering the connection part in the testing process. Therefore, as to the left atrial appendage occluder with an elastic waist in the seventh embodiment, it can be tested by any one of the above methods, and the testing result is the same as that with a non-elastic waist, which will not be repeated herein.

Third Exemplary of Deformation Capacity Testing Method

This testing method is substantially identical with the above-mentioned second exemplary deformation capacity testing method, that is, both of which are to represent the axial deformation capacity of a part by testing the axial displacement of the part under the same action of an axial force, with the part (the fixing part or the sealing part) being partially constrained. The difference between the two methods is that when the axial force is applied, the fixing parts in the two methods are constrained in different manners, and the sealing parts in the two methods are also constrained in different manners, and the occluders in particular embodiments will be illustrated below.

The third exemplary deformation capacity testing method may be used to test the left atrial appendage occluder 200 of the first embodiment, wherein the fixing part 210 and the sealing part 220 are tested individually. For example, only an individual fixing part 210 or only an individual sealing part 220 is tested each time.

Referring to FIG. 33, in the process of testing the fixing part 210, the annular clamping component 76 is used to clamp the fixing part 210 at the maximum radial contour of the fixing part 210 in the circumferential direction. The annular clamping component surrounds the central axis 2 and is perpendicular to the central axis 2, and the maximum radial contour of the fixing part 210 is in the hung zone 212 thereof; in the clamping process, the radial size of the clamped position of the fixing part 210 is smaller than the size of the fixing part 210 at a naturally expanded state. The fixing part 210 is radially compressed at the clamped position, for instance, the maximum radial length of the compressed fixing part being 80% of that uncompressed, and of course, other possible compression proportions can also be adopted but not listed one by one. For example, a radial force F0 may be applied to the annular clamping component 76, and the fixing part 210 is radially compressed. An axial force F2 is applied along the central axis 2 and towards the direction of the sealing part 220 at the end portion 214, which is connected with the connection part, of the fixing part 210, and the end portion 214 does not generate elastic deformation in the process that the axial force F2 is applied. The axial displacement ΔO3 of the projection O3 of the end portion 214 on the central axis along with the F2 is measured, and the ΔO3 is used to represent the deformation (or the deformation capacity) of the fixing part 210 in the third testing method.

It can be seen from the above that, after the left atrial appendage occluder is implanted into a human body with the fixing part 210 partially clamped, for example, the fixing part 210 in the first embodiment clamped at the maximum contour, the measured axial displacement with the application of the axial pull force shows the deformation capacity of the fixing part 210 which is implanted into the cavity of the left atrial appendage and pulled by the sealing part 220 with the restraint of the cavity of the left atrial appendage. With the same axial pulling force, the larger the ΔO3 is, the more easily the fixing part 210 tends to deform.

Referring to FIGS. 34 and 35, the sealing part 220 in the first embodiment comprises a proximal end disc surface 221, a distal end disc surface 222, and a distal end tip 224 which is on the distal end disc surface 222, wherein the connection part is connected with the distal end tip 224. In the process of independently testing the sealing part 220, the annular fixing part 77 is used to abut a disc surface at the maximum edge of the disc surface of the sealing part 220 and towards the fixing part 210, and meanwhile, the axial force F2 is applied along the central axis 2 and towards the fixing part 210 at the distal end tip 224. In the axial pulling process of the force F2, the position of the abutted disc surface by the annular fixing part 77 maintains unchanged in the direction of the central axis 2, and therefore the displacement ΔO4 of a projection of the distal end tip 224 on the central axis 2 is tested.

The sealing part 220 has different shapes, so that in the testing process, the abutting positions of the annular fixing part 77 are also different, and in general, the annular fixing part 77 abuts against the maximum radial edge of the sealing part 220 and towards the fixing part. For example, referring to FIG. 34, the proximal end disc surface 221 and the distal end disc surface 222 are parallel and identical in size, and the disc surface, towards the fixing part, of the sealing part 220 is the distal end disc surface 222, and therefore in the testing process, the annular fixing part 77 abuts against the maximum radial edge of the distal end disc surface 222. Referring to FIG. 35, the distal end disc surface 222 takes the shape of a step, and therefore in the testing process, the size of the annular fixing part 77 needs to be reasonably selected making sure that the annular fixing part 77 can completely join to and abut against the maximum radial edge of the distal end disc surface 222.

It can be seen from the above that, after the left atrial appendage occluder is implanted into a human body, a part of the sealing part is blocked by the cavity wall of the left atrium at the opening of the left atrial appendage, wherein at least the maximum radial edge, towards the fixing part, of the sealing part is blocked. Therefore, in the process of testing the sealing part, under the conditions that the annular fixing part abuts against the sealing part towards the maximum radial edge of the fixing part, and preventing the sealing part from generating displacement in the direction of the central axis 2, the tested axial displacement of the sealing part with the application of the axial pulling force shows the deformation capacity of the sealing part which is implanted into the cavity of the left atrial appendage and pulled by the sealing part. With the same axial pulling force, the larger the ΔO4 is, the more easily the fixing part tends to deform.

As measured from the third exemplary capacity testing method, with the application of the same axial force (F2), the axial displacement ΔO3 of the fixing part is less than the axial displacement ΔO4 of the sealing part. It can be understood that, when the fixing part and the sealing part are mutually pulled, the one with a greater axial displacement may be pulled dominantly by the other one. For example, under the same action of an axial force, the axial displacement of the fixing part according to the embodiment of the present disclosure is less than that of the sealing part, so that the fixing part may pull the sealing part dominantly in the mutual pulling process, and the sealing part deforms towards the fixing part (or the distal end). Such deformation makes the sealing part more tightly pressed to the wall of the left atrium at the opening of the left atrial appendage compared with a naturally expanded state, thereby improving the sealing effect of the sealing part on the opening of the left atrial appendage, and avoiding the formation of a gap between the sealing part and the wall of the left atrium, thereby preventing blood from flowing into the cavity of the left atrial appendage and preventing thrombi from flowing into the left atrium through the gap. Meanwhile, the fixing part dominating the pulling is not easily pulled away from the cavity wall of the left atrial appendage by the sealing part. Therefore, the occluder is more firmly fixed in the left atrial appendage, preventing the occluder from being disengaged from the left atrial appendage.

In the same way, it is possible to adopt the same third exemplary deformation capacity testing method to test the left atrial appendage occluders in other embodiment, for example, the sealing parts of the left atrial appendage occluders in the second to fourth embodiments are identical with the sealing part of the left atrial appendage occluder in the first embodiment, all of which include a dual-layer disc respectively, and therefore, it is possible to adopt the same testing method as the one in the first embodiment to test the deformation capacity of the sealing part.

The left atrial appendage occluder 500 in the first to fifth embodiments is typically formed integrally, for example, by integral braiding or integral cutting. Therefore, it is impossible to separate one of the parts in the testing process. For example, when the fixing part 610 is tested, it is impossible to independently separate the sealing part 620 therefrom, vice versa. Therefore the testing method with regard to the occluder 500 in the fifth embodiment is slightly different from that in the first to fourth embodiments, but the testing principles are identical.

Referring to FIG. 36, in the process of testing the fixing part 610, the annular clamping component 76 is adopted to circumferentially clamp the fixing part 610 at the maximum radial contour of the fixing part 610. The annular clamping component 76 surrounds the central axis 2 and is perpendicular to the central axis 2, and the maximum radial contour of the fixing part 610 is in the hung zone thereof. Meanwhile, another annular clamping component 74 is adopted at the connection part 630 to axially clamp the connection part 630, and in the clamping process the radial size of the connection part 630 is basically unchanged and its elastic deformation may be substantially ignored. An axial force F2 is applied onto the annular clamping component 74 along the central axis 2 and away from the fixing part 610. The axial displacement ΔO3 of the projection O3 of the position, where the axial force F2 is applied on the clamping component 74, is measured on the central axis 2 along with F2. The ΔO3 can represent the deformation (or deformation capacity) of the fixing part 610 in the third testing method.

The difference between the sealing part 620 in the fifth embodiment and the sealing part 620 in the first embodiment lies in that the distal end disc surface of the sealing part 620 comprises an opening at which the connection part 630 is connected to the distal end disc surface. In the testing process, referring to FIG. 37, the testing method in the fifth embodiment is the same as the testing method in the first embodiment in that an annular fixing part 77 is adopted to abut against the maximum radial contour of the distal end disc surface without deformation along the central axis 2 in the axial pulling process. The difference from the testing method in the first embodiment is that the clamping component 74 is used to clamp the connection part 630 which does not generate elastic deformation in the clamping process. Then, an axial force F2 is applied to the clamping component 74 along the central axis 2 and towards the fixing part. In the axial pulling process of F2, the position of the abutted disc surface along the central axis 2 remains unchanged with the annular fixing part 77, and therefore the displacement ΔO4 of a projection of the clamping component 74 on the central axis 2 is tested. It may be measured that, with the application of the same axial force (F2), the axial displacement ΔO3 of the fixing part is less than the axial displacement ΔO4 of the sealing part.

Referring to FIG. 38, the sealing part 720 in the sixth embodiment is a single-layer disc, for example, including a sealing disc surface 721 and fixed connection component 722, and the testing method thereof is identical with that of the sealing part 720 in the first embodiment. That is, the annular fixing part 77 is adopted to abut against the disc surface at the maximum edge of one side of the sealing disc surface 721 toward the fixing part. Meanwhile, an axial force F2 is applied to the fixed connection component 722 along the central axis 2 and towards the fixing part. In the axial pulling process of F2, the position of the abutted disc surface along the central axis 2 remains unchanged with the annular fixing part 77, and therefore the displacement ΔO4 of a projection of the fixed connection component on the central axis 2 is tested. The fixing part of the sixth embodiment may be any structure of the first to fifth embodiments, and therefore the testing process of the fixing part will not be repeated herein. It may also be measured that, under the same action of an axial force (F2), the axial displacement ΔO3 of the fixing part is less than the axial displacement ΔO4 of the sealing part.

When the third exemplary deformation capacity testing method is used to test the left atrial appendage occluder, each of the fixing part and the sealing part is tested individually. For example, only an individual fixing part or an individual sealing part is tested each time without considering the connection part in the testing process. Therefore, as to the left atrial appendage occluder with an elastic waist in the seventh embodiment, it can be tested by any one of the above methods, and the testing result is the same with the one without an elastic waist, which will not be repeated herein.

Figure 1A:
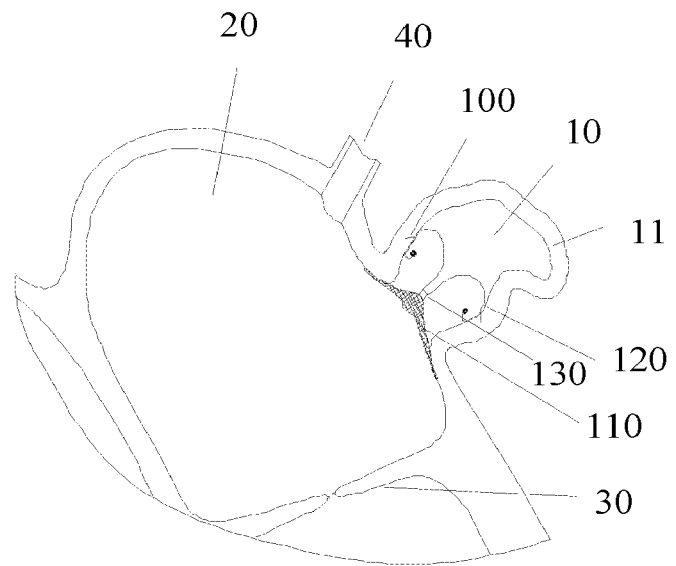
FIG. 1a illustrates a schematic diagram of the exemplary left atrial appendage occluder implanted into the left atrial appendage according to the first embodiment of the present disclosure.
Figure 2A:
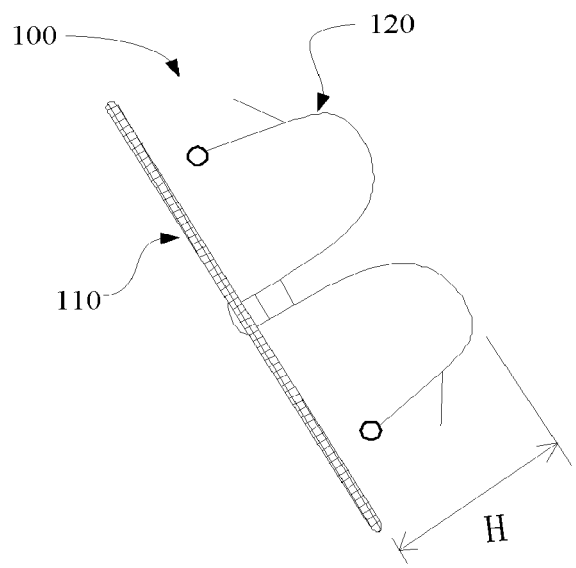

FIG. 1a shows a schematic diagram of a particular structure 100 of the left atrial appendage occluder 200 implanted into a left atrial appendage according to the first embodiment of the present disclosure. The left atrial appendage 10 is in the left atrium 20 and between the mitral valve 30 and the left superior pulmonary vein 40. Referring to FIGS. 1a and 2a, the left atrial appendage occluder 100 includes a sealing part 110, a fixing part 120 at one side of the sealing part 110, and a connection part 130 for connecting the sealing part 110 and the fixing part 120. The fixing part 120 is implanted into the cavity 10 of the left atrial appendage and is fixedly attached to the cavity wall 11 of the left atrial appendage 10, and the sealing part 110 covers and seals the opening of the left atrial appendage 10 so as to prevent blood from flowing therein.

Referring to FIG. 2a, in the natural state (i.e., in the absence of external force), the relative distance H between the proximal end of the sealing part 100 and the distal end of the fixing part 120 is 4-70 mm to meet the size of the anatomy structure of the left atrial appendage so as to ensure secure fixation. Specifically, the relative distance H is the one between a flat surface, where the closest proximal end of the sealing part 110 is in and which is perpendicular to the central axis line 140, and another flat surface where the farthest distal end of the fixing part 120 is in and which is perpendicular to the central axis line 140. The expanding diameter of the sealing part 110 and that of the fixing part 120 match to some requirements, and generally the expanding diameter of the sealing part 110 is greater than that of the fixing part 120 by about 1-40 mm to fit the different sizes of the anatomical structures of the left atrial appendage. The expanding diameter herein refers to the maximum circumferential diameter of each part when the occluder 100 releases and expands.

When the fixing part 120 is implanted into the cavity of a left atrial appendage, particularly deeply into the left atrial appendage by slightly stretching the left atrial appendage occluder 100 in the axial direction, the fixing part 120, on the one hand, will deform to adapt to the shape of the cavity of the left atrial appendage so as to be secured to the cavity wall of the left atrial appendage, and on the other hand, will flexibly deform as the left atrial appendage moves itself. However, the fixing part 120 and the sealing part 110 are restrained by the connection part 130, and therefore, in the above process, the fixing part 120 will pull the sealing part 110, thereby making the sealing part deform or slightly displace. In an embodiment of the present disclosure, since the sealing part 110 has stronger deformation capacity than the fixing part 120, in the process of pulling, the sealing part 110 is easier to deform so as to be adjoined and better attached to the opening of the left atrial appendage, thus promoting the sealing effect of the sealing part 110 on the basis of the inherent structure of the occluder 100. Meanwhile, the sealing part 110 is easy to deform, which correspondingly can reduce abrasion to tissues at the opening of the left atrial appendage and reduce the possibility of inflammations, pericardial effusion or even cardiac tamponade.

Figure 3A:
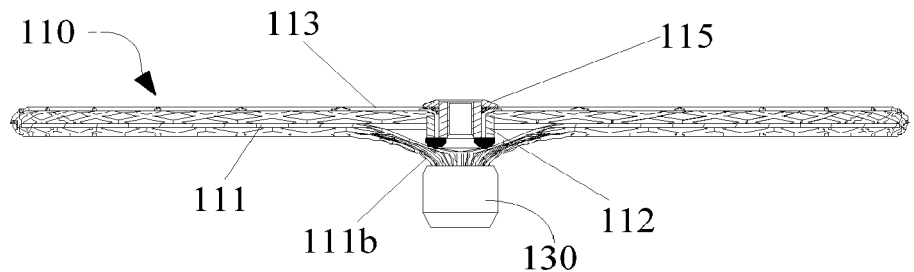
Figure 4A:
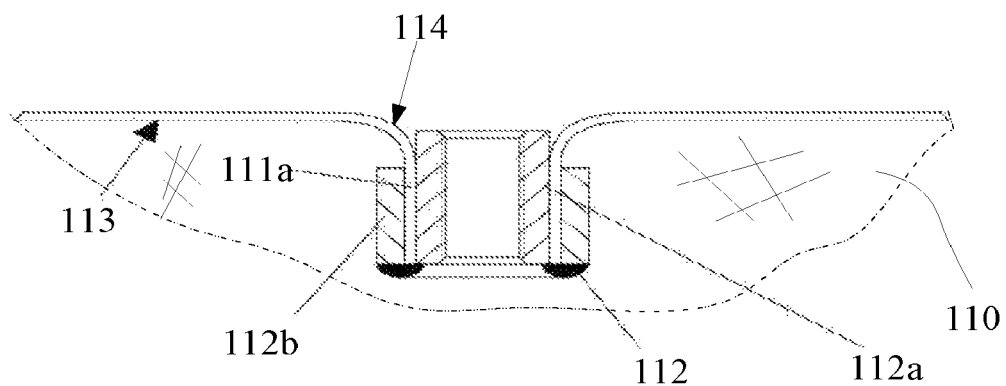

Referring to FIGS. 3a and 4a, the sealing part 110 includes a plurality of braid wires 111 and a fixed connection component 112, wherein the plurality of braid wires 111 may be nickel-titanium metal wires or polymeric biocompatible wires, which are braided into disc-shaped braided bodies. For example, the diameter of metal wires is 0.01-0.5 mm and the number of metal wires may be chosen from 12 to 168, or from 36 to 144, particularly, wherein an even number of metal wires may be chosen. The metal wires may be rationally allocated in diameter and number, and subjected to heat processing. The metal wires may also be coated with a bioceramic film so that the sealing part 110 has a suitable hardness so as to maintain a certain rigidity.

The distal ends 11b of a plurality of braid wires 111 are all accommodated and fixed by the connecting component 130 and the proximal ends 11a of the braid wires are all accommodated and fixed by the fixed connection component 112, thus forming a closed braided body. For example, the fixed connection component 112 in the Figure includes an inner tube 112a and an outer tube 112b in a nested configuration, with a gap left between the inner tube 112a and the outer tube 112b. All the proximal ends 111a of the plurality of braid wires 111 are accommodated in the gap and are fixed with the fixed connection component 112, such as, by welding. The inner surface of the inner tube 112a may comprise internal screws to connect a conveyer.

In terms of the structure, the sealing pan 110 includes a disc-shaped portion 113 adjoined to the fixed connection component 112, and a transition portion 114 extending between the disc-shaped portion 113 and the proximal end of the fixed connection component 112, the disc-shaped portion 113 and the transition portion 114 being different regions of the same braided body. The expanded volume of the disc-shaped portion 113 may define the entire expanded volume diameter of the entire sealing part 110. The braid wires 111 of the transition portion 114 are bent so that the proximal ends 111a of the braid wires 111 may be accommodated into the fixed connection component 112 while the transition portion 114 covers at least part of the fixed connection component 112. For example, the transition portion 114 in the figures substantially covers the proximal end annular circumferential face of the fixed connection component 112.

Figure 5A:
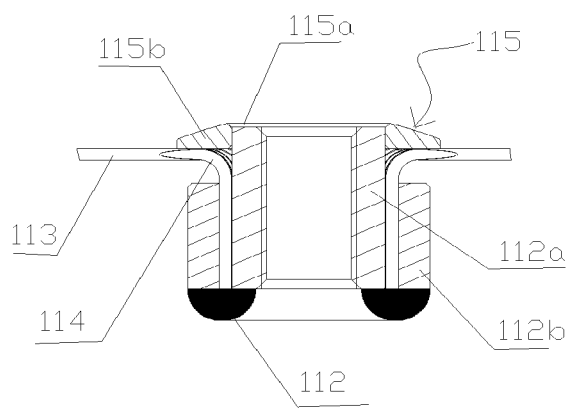
Figure 6A:
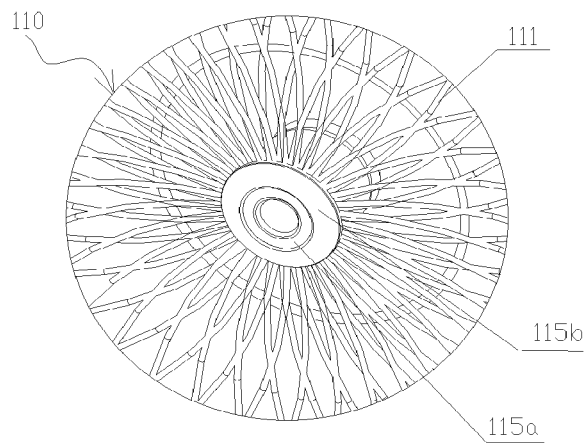

The braid wires 111 of the transition portion 114 in bent arrangement tend to form a wavy surface structure, which is rather rough, and when the sealing part 110 is taken into a sheath tube, this structure may damage the tip end of the sheath tube, or it is also possible that the sealing part 110 cannot be sheathed, thereby leading to surgical failure, so therefore, the sealing part 110 also comprises a sealing cap 115 to cover the transition portion 114. Referring to FIGS. 3a, 5a and 6a, the sealing cap 115 includes an end cap 115a, and a sidewall 115b connected to the end cap 115a, and the end cap 115a may fixedly cover a part of the fixed connection component 112. For example, the end cap 115a in the figures is of an annular structure to fixedly cover the proximal side of the inner tube 112a and keeps the inner tube 112a unobstructed to not hinder the connection between the fixed connection component 112 and the conveyer. The sidewall 115b is connected to the end cap 115a in a smooth transition, and the sidewall 115b extends along the proximal end to the distal end in the form of an arc to ensure the coverage of the transition portion 114 of the sealing part 110. Further, the equivalent diameter (or referred to as the maximum circumferential diameter) of the sealing cap 115 should be less than the inner diameter of the sheath tube of the conveyer, such that the occluder 100 can be assembled in the sheath tube smoothly; and the equivalent diameter may be 2-5 mm, corresponding to a 6F-15 sheath tube.

The sealing cap 115 may substantially cover the wavy structure formed by the tight arrangement of the braid wires III in the transition portion 114 in order to maintain smoothness here. When the sealing part 110 is assembled into the sheath tube, it can play a guiding role and reduce friction, thus reducing the damage to the sheath tube tip end and improving the success rate of surgery; and simultaneously, upon the implantation of the occluder 100, creeping of the endothelial cells may be promoted and the risk of thrombi formed by long-term blood on the sealing part 110 is reduced.

Figure 7A:
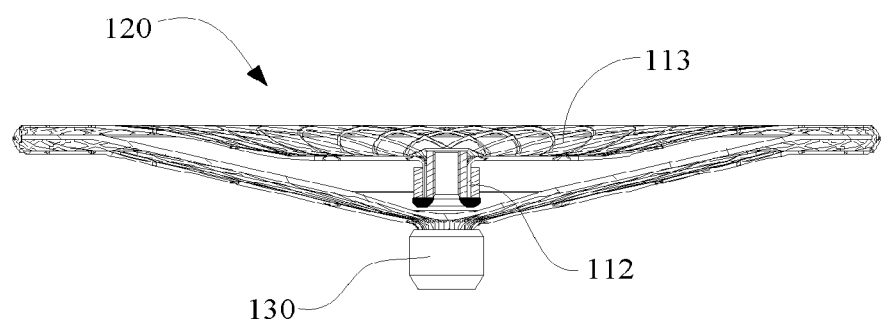
FIG. 7a is a schematic diagram of a disc-shaped portion which is a concave surface.
Figure 8A:
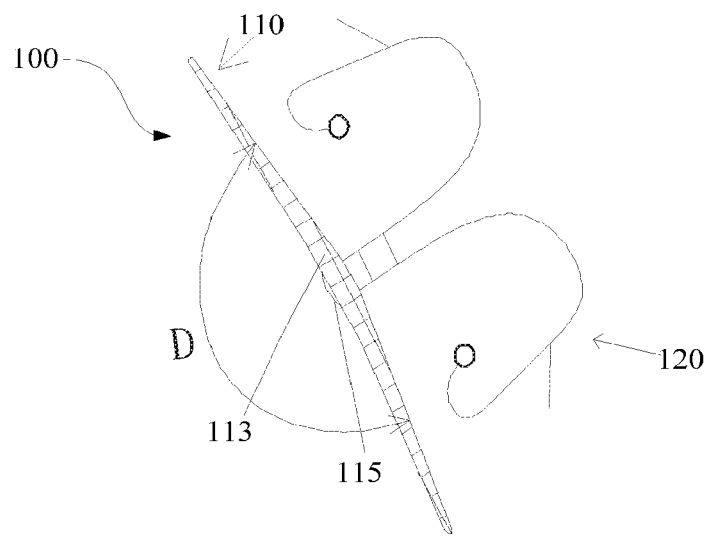
FIG. 8a is a schematic diagram of a disc-shaped portion which is a concave surface.
Figure 9A:
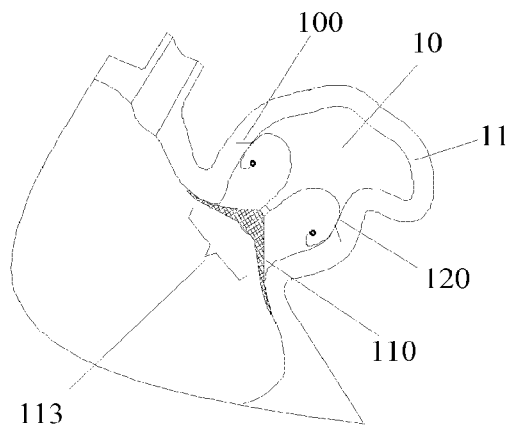
FIG. 9a is a schematic diagram of the left atrial appendage occluder, in which the disc-shaped portion is a concave surface, implanted into the left atrial appendage.

Referring to FIG. 3a, the proximal end surface of the disc-shaped portion 113 of the sealing part 110 may be a flat surface. Referring to FIGS. 7a and 8a, the proximal end surface of the disc-shaped portion 113 of the sealing part 110 may be a concave surface, and the equivalent concave surface angle D of the concave surface is less than 180 degrees, and the equivalent concave surface angle may be a conical surface angle when the concave surface is a conical surface, or a conical surface angle of an imaginary conical surface formed by the concave surface and an extension surface thereof. Referring to FIG. 9a, when the sealing part 110 is pulled by the fixing part 120 to be attached tightly to the opening of the left atrial appendage 10, the concave surface may better adapt to the anatomical shape of the opening of the left atrial appendage, so as to facilitate the optimal sealing effect.

Figure 10A:
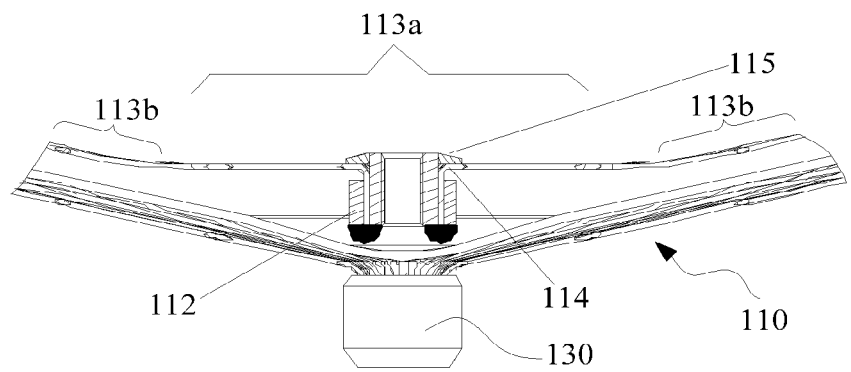
FIG. 10a is a schematic diagram of an implementation method when the disc-shaped portion is a concave surface.

The structure of the concave surface can be varied. For instance, it may be a single conical surface structure, and the equivalent concave surface angle is the conical surface angle; or the concave surface can be formed by combination of a plurality of surfaces, as long as the formation of a proper effective concave surface angle is guaranteed, and at this time, the equivalent concave surface angle is the conical surface of the imaginary conical surface formed by the concave surface and the extension surface thereof. For example, referring to FIG. 10a, the disc-shaped portion 113 comprises a first flat surface 113a adjoined to the fixed connection component 112, and an inclined surface 113b which is connected with the first flat surface 13a, wherein the first flat surface 113a and the inclined surface 113b are in smooth continuous transition. The first flat surface 113a is adjoined to the fixed connection component 112, and that is connected with a transition component, and the first flat surface 113a may be an annular structure surrounding the transition component 114 (or the fixed connection component 112) in shape. The so-called "flat surface" refers to a flat surface which is substantially perpendicular to the central axis line 140 of the occluder 100. The inclined surface 113b may be of an annular structure surrounding the first flat surface 113a, and is not parallel to the "flat surface", and has an inclination angle; and the concave surface angle is formed by the conical surface angle of the equivalent conical surface formed by the annular inclined surface 113b and the extension surface thereof, and is less than 180 degrees.

In the process that the fixing part 120 pulls the sealing part 110 through the connection part 130, the single conical surface structure is more likely to radially contract and deform towards the inner part of the left atrial appendage, so that the effective occlusion diameter is shortened, and the sealing part 110 cannot completely and effectively cover the opening of the left atrial appendage. While the disc-shaped portion 113 comprises a plurality of surfaces, the first flat surface 113a is correspondingly arranged at the connection part 130, and the flat surface structure is not likely to radially contract and deform, so that the effective occlusion diameter is ensured. On the other hand, the inclined surface 113b surrounding the first flat surface 113a can better adapt to the anatomical shape of the opening of the left atrial appendage, and the optimal sealing effect is realized.

Figure 11A:
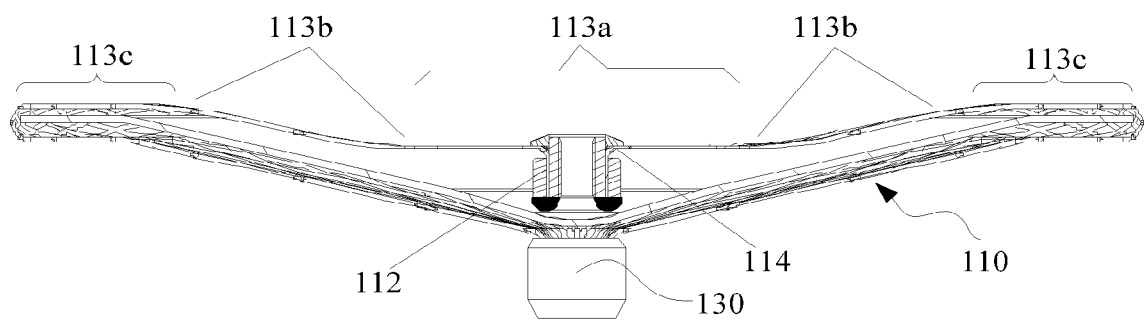
FIG. 11a is a schematic diagram of another implementation method when the disc-shaped portion is a concave surface.

Referring to FIG. 11a, in another implementation of the present disclosure, the disc-shaped structure comprises a first flat surface 113a which is adjoined to the fixed connection component 112, an inclined surface 113b which is connected with the first flat surface 113a, and a second flat surface 113c which is connected with the inclined surface 113b, wherein the first flat surface 113a and the inclined surface 113b are in smooth continuous transition, and the inclined surface 113b and the second flat surface 113c are in smooth continuous transition. The first flat surface 113a and the inclined surface 113b are configured in the same manner as in FIG. 10a, and will not be described in greater detail herein. In the same way, the second flat surface 113c is a "flat surface" structure which is substantially perpendicular to the central axis line 140 of the occluder 100, and forms an inclination angle with respect to the inclined surface 113b. The second flat surface 113c may be an annular structure surrounding the inclined surface 113b structurally. Here, the concave surface angle is formed by the conical surface angle of the equivalent conical surface formed by the inclined surface 113b and the extension surface thereof, and is similarly less than 180 degrees. The second flat surface 113c adapts to the structure of the connection part of the left atrial appendage and the left atrium 20, so that the optimal joint is achieved; and the integrally smooth surface may also be formed on the surface of the left atrium 20 and other parts of the left atrium 20, so that blood flow is facilitated, and meanwhile, the risk of thrombi is reduced.

Figure 12A:
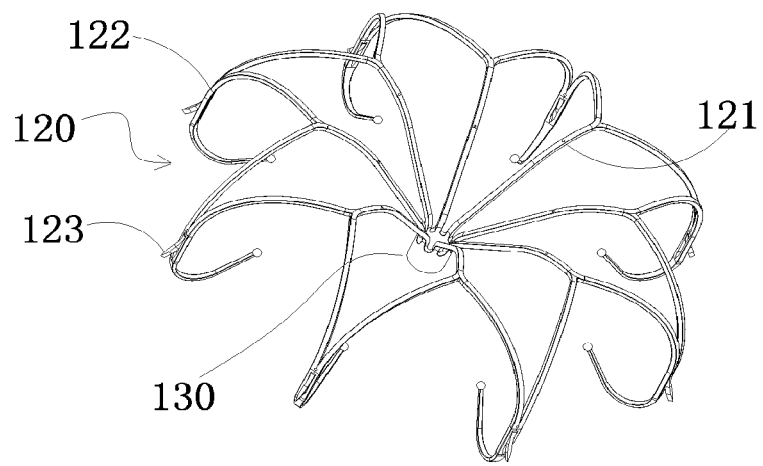
FIG. 12a is a schematic diagram of a fixing part of the left atrial appendage occluder in FIG. 1b.

Referring to FIG. 12a, the fixing part 120 comprises a plurality of supporting parts 121, wherein each end of the supporting members 121 is fixedly connected with the connection part 130, and the other end comprises a hung bearing section 122. In manufacturing, a metal tube (such as the nickel-titanium tube) of which the diameter is 0.25-5 mm may be divided into at least one fixing frame supporting members 121, and an end portion fixedly connected with the connection part 130 is reserved and then molded into a predetermined shape by heat processing, so that the fixing part 120 is formed. Alternatively, at least one metal wire (such as nickel-titanium wires) of which the diameter is 0.1-1.5 mm, or at least one metal sheet (such as nickel-titanium sheets) of which the width is 0.1-0.8 mm and the thickness is 0.05-0.5 mm, are molded into the predetermined shapes by heat processing, so that the fixing part 120 is formed.

Figure 13A:
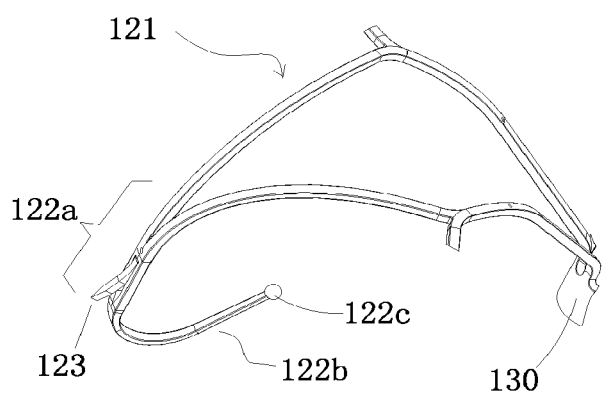

Referring to FIG. 13a, the hung bearing section 122 comprises a bearing portion 122a and a bent tail portion 122b which is connected with the bearing portion 122a, wherein the bearing portion 122a is usually of a rod-shaped structure, and is attached and fixed to the cavity wall of the left atrial appendage; the bent tail portion 122b is formed by smoothly bending from the bearing portion 122a, the bending shape is approximately shaped as a U or a V to reduce the damage of the occluder 100 to the cavity wall of the left atrial appendage during the surgical procedure. Meanwhile, the bent portion can be clamped within the pectinate muscles of the cavity wall of the left atrial appendage to improve the fixing capacity of the left atrial appendage occluder 100. The tail end of the tail portion 122b may also be set to be of a spherical structure 122c, so that the damage to the wall of the left atrial appendage is further reduced.

Figure 14A:
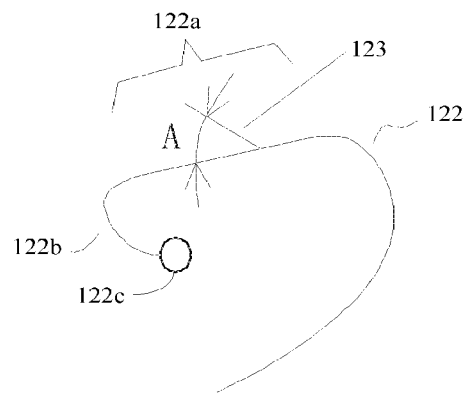
FIG. 14a is a schematic diagram of an anchor.

Referring to FIG. 14a, the anchor 123 facing the sealing part 110 is arranged on the hung bearing section 122, is specifically arranged on the bearing portion 122a, and is used for piercing into the cavity wall of the left atrial appendage so as to further fix the occluder 100. An angle A is formed between the anchor 123 and the bearing portion 122a, with the angle A ranging from 0 degree to 90 degrees, so that the anchor 123 can pierce into but not puncture the cavity wall of the left atrial appendage, and achieve a better fixing effect.

Figure 15A:
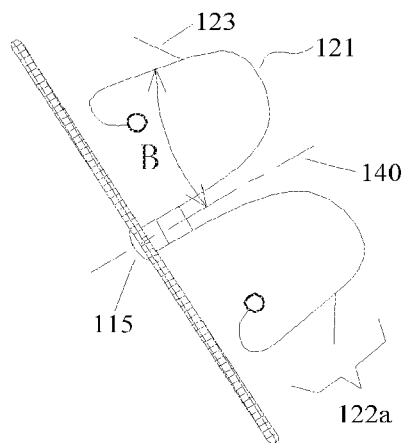
FIG. 15a is a schematic diagram of an inclined angle between a bearing portion and an central axis line of the left atrial appendage occluder.
Figure 16A:
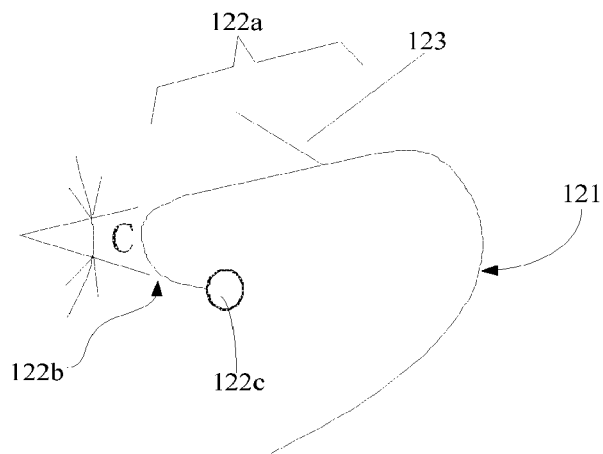
FIG. 16a is a schematic diagram of a bend angle of a tail portion.

Referring to FIG. 15a, an angle B is formed between the bearing portion 122a and the central axis line 140 of the left atrial appendage occluder 100, with the angle B ranging from 0 degree to 85 degrees, so that the bearing portion 122a may cling more effectively to the cavity wall of the left atrial appendage, and furthermore a certain supporting force is provided for the anchor 123 to pierce into the cavity wall of the left atrial appendage. Meanwhile, this arrangement ensures that the anchor 123 cannot puncture the cavity wall, and the left atrial appendage occluder 100 is firmly fixed in the left atrial appendage. Referring to FIG. 16a, the bend angle of the tail portion 122b is an angle C which refers to an angle formed by an imaginary extension line of the bearing portion 122a and an imaginary extension line of a linear segment of the tail portion 122b, and the angle C ranges from 0 degree to 180 degrees, so that the damage of the occluder 100 to the wall of the left atrial appendage during a surgical procedure is reduced as much as possible.

In conclusion, in the left atrial appendage occluder according to the embodiments of the present invention, the deformation capacity of the sealing part is configured to be greater than the deformation capacity of the fixing part, so as to avoid the situation in which the sealing part cannot be optimally fitted with the opening of the left atrial appendage when the fixing part is placed inside of the left atrial appendage, thereby enhancing the occlusion effect. Meanwhile, owing to the great deformation capacity of the sealing part, risks of abrasion or break of the opening of the left atrial appendage by the sealing part may be reduced. Furthermore, the sealing cap disposed on the surface of the proximal end surface of the sealing part is capable of substantially covering the wavy structure formed by the densely arranged braid wires in the transition portion to maintain a smooth surface, thereby reducing damage to the tip of the sheath tube, and also accelerating growth of endothelial cells after the occluder has been implanted, as well as reducing the risk of thrombopoiesis on the sealing part due to long-term blood.

The invention claimed is:

1. A left atrial appendage occluder, comprising:
a sealing part having a disc-shaped portion, a transition portion and a fixed connection component, the fixed connection component having a proximal end;
wherein the transition portion extends between the disc-shaped portion and the proximal end of the fixed connection component;
a flat sealing cap covering the transition portion and fixed to the proximal end of the fixed connection component;
a fixing part disposed at one side of the sealing part and having a connection end;
a connection part that connects the sealing part and the connection end of the fixing part, the connection part having a distal end and a proximal end;
wherein the fixing part comprises a concave zone formed by radially extending from the connection end in a distal direction away from the sealing part, and a hung zone formed by extending in a proximal direction from the concave zone towards the sealing part, with the hung zone having an edge that defines an opening that faces towards the sealing part, and wherein an edge zone extends from the edge of the hung zone towards the connection part;
wherein at least a part of the edge zone is generally parallel to the sealing part; and
wherein the fixed connection component and the flat sealing cap are separate.

2. The left atrial appendage occluder of claim 1, wherein at least a part of the disc-shaped portion is flat.

3. The left atrial appendage occluder of claim 2, wherein the disc-shaped portion adjacent to the transition portion is flat.

4. A left atrial appendage occluder, comprising:
a sealing part having a disc-shaped portion, a transition portion and a fixed connection component, the fixed connection component having a proximal end;
wherein the transition portion extends between the disc-shaped portion and the proximal end of the fixed connection component; and
a flat sealing cap covering the transition portion and fixed to the proximal end of the fixed connection component;
wherein the fixed connection component has an inner tube and an outer tube in a nested configuration, the inner tube and the outer tube both having a proximal end, and a gap formed between the proximal end of the inner tube, the proximal end of the outer tube and the flat sealing cap.

5. The left atrial appendage occluder of claim 4, further comprising:
a fixing part disposed at one side of the sealing part and having a connection end; and
a connection part that connects the sealing part and the connection end of the fixing part, the connection part having a distal end and a proximal end.

6. The left atrial appendage occluder of claim 5, wherein the fixing part comprises a concave zone formed by radially extending from the connection end in a distal direction away from the sealing part, and a hung zone formed by extending in a proximal direction from the concave zone towards the sealing part, with the hung zone having an edge that defines an opening that faces towards the sealing part, and wherein an edge zone extends from the edge of the hung zone towards the connection part.

7. The left atrial appendage occluder of claim 6, wherein the connection part defines a central axis, and wherein the opening has a cross-section that is perpendicular to the central axis.

8. The left atrial appendage occluder of claim 6, wherein the hung zone is provided with at least one anchor facing the sealing part; and an inclined angle between each anchor and the hung zone ranges from 0 degree to 90 degrees.

9. The left atrial appendage occluder of claim 6, wherein at least a part of the edge zone is generally parallel to the sealing part.

10. The left atrial appendage occluder of claim 6, wherein an inclined angle between the hung zone and a central axis line of the left atrial appendage occluder ranges from 0 degree to 85 degrees; and an equivalent bend angle of the edge zone ranges from 0 degree to 180 degrees.

11. The left atrial appendage occluder of claim 5, wherein the sealing part and the fixing part both have a radial deformation capacity and an axial deformation capacity, and wherein the radial deformation capacity of the sealing part is greater than that of the fixing part, and/or the axial deformation capacity of the sealing part is greater than that of the fixing part.

12. The left atrial appendage occluder of claim 5, wherein the sealing part and the fixing part both have a radial length variation and a radial length variation ratio, wherein with the application of a same radial force, the radial length variation of the sealing part is greater than the radial length variation of the fixing part, or the radial length variation ratio of the sealing part is greater than the radial length variation ratio of the fixing part.

13. The left atrial appendage occluder of claim 5, wherein with the application of the same axial force, a displacement of the sealing part along a direction of the axial force is greater than a displacement of the fixing part along the direction of the axial force.

14. The left atrial appendage occluder of claim 5, wherein the sealing part has a proximal end and the fixing part has a distal end, wherein a relative distance between the proximal end of the sealing part and the distal end of the fixing part is 4-70 mm.

15. The left atrial appendage occluder of claim 5, wherein each of the sealing part and the fixing part has an expanding diameter, and wherein the expanding diameter of the sealing part is greater than the expanding diameter of the fixing part.

16. The left atrial appendage occluder of claim 5, wherein the fixing part comprises a plurality of supporting members, each supporting member having a first end and a second end, with the first end of each of the supporting members fixedly connected to the connection part respectively and the second end of each supporting member includes a hung bearing section, and wherein at least one hung bearing section is provided with an anchor facing the sealing part; and an inclined angle between the anchor and the hung bearing section ranges from 0 degree to 90 degrees.

17. The left atrial appendage occluder of claim 16, wherein at least a part of the hung bearing section is generally parallel to the sealing part.

18. The left atrial appendage occluder of claim 16, wherein the hung bearing section comprises a bearing portion and a bent tail portion connected to the bearing portion.

19. The left atrial appendage occluder of claim 18, wherein an inclined angle between the bearing portion and a central axis line of the left atrial appendage occluder ranges from 0 degree to 85 degrees; and an equivalent bend angle of the end portion ranges from 0 degree to 180 degrees.

20. A left atrial appendage occluder, comprising:
- a sealing part having a disc-shaped portion, a transition portion and a fixed connection component, the fixed connection component having a proximal end;
- wherein the transition portion extends between the disc-shaped portion and the proximal end of the fixed connection component; and
- a flat sealing cap covering the transition portion and fixed to the proximal end of the fixed connection component;
- wherein the fixed connection component has an inner tube which has a proximal side, and wherein the flat sealing cap includes an end cap and a sidewall which is connected to the end cap, and the end cap has an annular structure to fixedly cover the proximal side of the inner tube.

* * * * *